(12) United States Patent
Siprashvili et al.

(10) Patent No.: US 12,385,010 B2
(45) Date of Patent: *Aug. 12, 2025

(54) GENE THERAPY FOR RECESSIVE DYSTROPHIC EPIDERMOLYSIS BULLOSA USING GENETICALLY CORRECTED AUTOLOGOUS KERATINOCYTES

(71) Applicants: The Board of Trustees of the Leland Stanford Junior University, Stanford, CA (US); The United States Government as represented by the Department of Veterans Affairs, Washington, DC (US)

(72) Inventors: Zurab Siprashvili, San Mateo, CA (US); Ngon T. Nguyen, Union City, CA (US); M. Peter Marinkovich, Redwood City, CA (US); Jean Tang, Stanford, CA (US); Alfred T. Lane, Los Altos, CA (US); Paul A. Khavari, Palo Alto, CA (US)

(73) Assignees: The Board of Trustees of the Leland Stanford Junior University, Stanford, CA (US); The United States Government as represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/933,687

(22) Filed: Oct. 31, 2024

(65) Prior Publication Data

US 2025/0075178 A1 Mar. 6, 2025

Related U.S. Application Data

(62) Division of application No. 16/066,253, filed as application No. PCT/US2017/012061 on Jan. 3, 2017, now Pat. No. 12,173,314.

(Continued)

(51) Int. Cl.
C12N 5/00 (2006.01)
A61K 48/00 (2006.01)
C12N 5/071 (2010.01)

(52) U.S. Cl.
CPC ........ C12N 5/0629 (2013.01); A61K 48/0058 (2013.01); A61K 48/0075 (2013.01);
(Continued)

(58) Field of Classification Search
CPC .......... C12N 5/00; C12N 5/06; C12N 5/0625; C12N 5/0629; C12N 5/063; C12N 2510/00; C12N 2760/16043
See application file for complete search history.

(56) References Cited

U.S. PATENT DOCUMENTS 5,830,725 A 11/1998 Nolan
12,110,504 B2 * 10/2024 Siprashvili .............. A61P 27/02
(Continued)

OTHER PUBLICATIONS

Siprashvili et al Long-Term Type VII Collagen Restoration to Human Epidermolysis Bullosa Skin Tissue, Human Gene Therapy 21: 1299-1310, 2010.*

(Continued)

*Primary Examiner* — Kevin K Hill
(74) *Attorney, Agent, or Firm* — Pamela J. Sherwood; Bozicevic, Field & Francis LLP

(57) ABSTRACT

Methods are provided for the cell-based delivery of collagen VII for the treatment of Epidermolysis Bullosa and corneal erosion. The disclosure also provides a composition and a pharmaceutical composition comprises, comprise, or alternatively consist essentially of, or yet further consist of a keratinocyte sheet or a corneal cell sheet.

17 Claims, 14 Drawing Sheets

Specification includes a Sequence Listing.

Related U.S. Application Data

(60) Provisional application No. 62/274,700, filed on Jan. 4, 2016, provisional application No. 62/414,533, filed on Oct. 28, 2016.

(52) U.S. Cl.
CPC ...... *A61K 48/0091* (2013.01); *C12N 2510/00* (2013.01); *C12N 2760/16043* (2013.01)

(56) References Cited

U.S. PATENT DOCUMENTS

| | | | | |
|---|---|---|---|---|
| 12,173,314 | B2* | 12/2024 | Siprashvili | ......... A61K 48/0075 |
| 2002/0090725 | A1 | 7/2002 | Simpson et al. | |
| 2008/0124356 | A1* | 5/2008 | Djian | ......... C12N 7/00 |
| | | | | 435/395 |
| 2019/0192636 | A1* | 6/2019 | Dailey | ......... A61K 38/39 |
| 2019/0382724 | A1* | 12/2019 | Siprashvili | ......... A61K 48/0091 |

OTHER PUBLICATIONS

Auxenfans et al, Cultured autologous keratinocytes in the treatment of large and deep burns: A retrospective study over 15 years, Burns 41: 71-79, 2015; available online Jul. 2, 2014.*

Mujaj et al, Serum-Free Primary Human Fibroblast and Keratinocyte Coculture Tissue Engineering 16(4): 1407-1420, 2010.*

Sugiyama et al, Decreased level of mitochondrial RNA by glutamate in cultured cortical neurons, Neurochemistry 18(8): 827-830, 2007.*

Chua et al, In vitro evaluation of fibrin mat and Tegaderm™ wound dressing for the delivery of keratinocytes—Implications of their use to treat burns, Burns 34: 175-180, 2008.*

Cutlar et al, Exp. Dermatology 23: 1-16, available online Sep. 23, 2013.*

Gach et al, Human Gene Therapy 15: 921-933, 2004.*

Titeux et al, Molecular Therapy 18(8): 1509-1518, 2010.*

Jackow et al, J. Invest. Dermatol. 136: 1346-1354, 2016.*

Mavilio et al, Nature Medicine 12(12): 1397-1402, 2006.*

Baldeschi et al. (2003) "Genetic correction of canine dystrophic epidermolysis bullosa mediated by retroviral vectors", Human Mol. Genetics 12(15): 1897-1905.

Bentley et al.(2001) "Morphology and Immunohistochemistry of Spontaneous Chronic Corneal Epithelial Defects (SCCED) in Dogs", Investigative Ophthalmology & Visual Science, vol. 42, No. 10, pp. 2262-2269.

Bibhuti et al., "Dystrophic Epidermolysis Bullosa", Journal of Perinatology, Jan. 1, 2004, pp. 41-47, vol. 24, No. 1, Nature Publishing Group, London, United Kingdom.

Bruckner-Tuderman, (2010) "Dystrophic epidermolysis bullosa: pathogenesis and clinical features" Dermatologic clinics, 28:1 107-114.

Chameettachal et al, Understanding Retroviral Life Cycle and its Genomic RNA Packaging, J. Mol. Biol. 435(3); e167924, 41 pages, doi.org/10.1016/j.jmb.2022.167924, Dec. 16, 2022.

Chen et al. (2006) "The cleavage plane of corneal epithelial adhesion complex in traumatic recurrent corneal erosion", Molecular Vision, 2006, vol. 12, pp. 196-204.

Chen et al, (2000) "Development and Characterization of a Recombinant Truncated Type VII Collagen Minigene", J. Bioi. Chem. 275(32): 24429-24435.

Coolen et al (2007) "Culture of Keratinocytes for Transplantation Without the Need of Feeder Layer Cells", Cell Transplantation 16: 649-661.

Corning® PureCoat™ Collagen I Mimetic Cultureware Product Sheet, Corning Life Sciences (2012).

Dellambra et al (2000) "Toward Epidermal Stem Cell-Mediated ex Vivo Gene Therapy of Junctional Epidermolysis Bullosa" Human Gene Therapy 11:16 :2283-2287.

Font et al (1994) "A new three-dimensional culture of human keratinocytes: optimization of differentiation", Cell Biology and Toxicology 10: 353-359.

Gache et al, (2004) "Construction of skin equivalents for gene therapy of recessive dystrophic epidermolysis bullosa" Human Gene Therapy 15: 921-933.

Gene Molecular, (2014) "Gene Targeting and Gene Correction III", American Society, vol. 22, Suppl.1 S218 No. 562.

He Lin, et al., (2013) "Clinical Genetics" Version 1, Shanghai Scientific and Technical Press, pp. 703-708.

Hou et al., "Intravenously Administered Recombinant Human Type VII Collagen Derived from Chinese Hamster Ovary Cells Reverses the Disease Phenotype in Recessive Dystrophic Epidermolysis Bullosa Mice", Journal of Investigative Dermatology, Dec. 2015, pp. 3060-3067, vol. 135, Issue 12, Elsevier, New York City, NY.

Hu et al, Design of Retroviral Vectors and Helper Cells for Gene Therapy, Pharmacological Reviews 52(4): 493-511, 2000.

Jackow et al. (2016) "Gene-Corrected Fibroblast Therapy for Recessive Dystrophic Epidermolysis Bullosa using a Self-Inactivating COL7A1 Retroviral Vector", J. Invest. Dermatol. 136: 1346-1354.

Kimoto et al., "Development of a Bioengineered Corneal Endothelial Cell Sheet to Fit the Corneal Curvature", Investigative Opthalmology & Visual Science, Apr. 11, 2014, p. 2337-2343, vol. 55. No. 4, The Association for Research in Vision and Ophthalmology, Inc. Rockville, MD.

Levy et al, (1998) "Optimised retroviral infection of human epidermal keratinocytes: long-term expression of transduced integrin gene following grafting on to SCID mice", Gene Therapy 5: 913-922.

Latella et al.,(2014), "Collagen VII Gene Delivery via an Adeno-Sleeping Beauty Transposon in COL7A1-Deficient Keratinocytes From Epidermolysis Bullosa Patients," Mol. Ther., vol. 22, Suppl. 1, S218 No. 562.

Liu et al, (2013) "Establishment of a novel method for primary culture of normal human cervical keratinocytes", Clin. Med. J. 126(17): 3344-3347.

Mavilio et al. (2006) "Correction of junctional epidermolysis bullosa by transplantation of genetically modified epidermal stem cells" Nature Medicine 12(12): 1397-1402.

Moloney Murine Leukemia Virus Fact Sheet; https://ehs.stanford.edu/reference/moloney-murine-leukemia-virus-fact-sheet; last visited Aug. 24, 2022.

Murauer et al., "Functional correction of type VII collagen expression in dystrophic epidermolysis bullosa." Journal of Investigative Dermatology, Jan. 2011, pp. 74-83, vol. 131, No. 1, Elsevier, New York City, NY.

Nayak et al (2013) "Skin Equivalent Tissue-Engineered Construct: Co-Cultured Fibroblasts/Keratinocytes on 30 Matrices of Sericin Hope Cocoons" PLoS ONE 8(9): e74779, 17 pages.

Okada et al. (1999) "Imaging cells in the developing nervous system with retrovirus expressing modified green fluorescent protein", Exp. Neural. 156: 394-406.

O'Keefe, Nucleic Acid Delivery: Lentiviral and Retroviral Vectors, Materials and Methods 3: 174, 18 pages, doi.org/10.13070/mm.en .3.174, original version 2013, last modified May 11, 2024.

Perdoni et al., "Gene editing toward the use of autologous therapies in recessive dystrophic epidermolysis bullosa", Translational Research, May 27, 2015, vol. 168, Elsevier, New York City, NY.

Perdoni et al. (2015) "Gene editing toward the use of autologous therapies in recessive dystrophic epidermolysis bullosa", Translational Research, May 27, 2015 vol. 168, pp. 50-58.

Sebastiano et al., "Human COL7A1-corrected induced pluripotent stem cells for the treatment of recessive dystrophic epidermolysis bullosa", Science Translational Medicine, Nov. 26, 2014, pp. 1-23, vol. 6, No. 264, American Association for the Advancement of Science, Washington, D.C.

Suerth et al, Self-inactivating Alpharetroviral Vectors with a Split-Packaging Design, J. Viral. 84(13): 6626-6635, 2010.

Siprashvili et al. (2010) "Long-Term Type VII Collagen Restoration to Human Epidermolysis Bullosa Skin Tissue", Human Gene Therapy, Oct. 1, 2010, vol. 21, No. 10, pp. 1299-1310.

Siprashvili et al., "Phase I clinical trial of genetically corrected autologous epidermal keratinocytes for recessive dystrophic

(56) References Cited

OTHER PUBLICATIONS epidermolysis bullosau", J Invest Dermatol., Jan. 1, 2014, p. 575, vol. 134. No. Suppl 1, Abstract 430, Nature Publishing Group, London, United Kingdom.

Siprashvili et al., Safety and Wound Outcomes Following Genetically Corrected Autologous Epidermal Grafts in Patients With Recessive Dystrophic Epidermolysis Bullosa, JAMA 3176(17): 1808-1817, doi:10.1001/jama.2016.15588, Nov. 1, 2016.

U.S. Department of Health and Human Services, Food and Drug Administration, Center for Biologics Evaluation and Research, (2000) Guidance for Industry, "Supplemental Guidance on Testing for Replication-Competent Retrovirus in Retroviral Vector-Based Gene Therapy Products and During Follow-up of Patients in Clinical Trials Using Retroviral Vectors" Human Gene Therapy, 12; pp. 315-320.

Watt et al, (2006) "Chapter 16—Cultivation and Retroviral Infection of Human Epidermal Keratinocytes", Cell Biology (Third Edition), Laboratory Handbook, vol. 1: 133-138.

Wei et al., "Keratinocyte cytoskeletalroles in cell sheet engineering", BMC Biotechnology, Feb. 26, 2013, pp. 1-10, vol. 13, No. 1, BioMed Central, London, United Kingdom.

Wu et al, Effect of Genome Size on AAV Vector Packaging, Molecular Therapy 18(1): 80-86, 2010.

Bennett et al. (2017) "Understanding capsid assembly and genome packaging for adeno-associated viruses" *Future Virology*, 12(6), pp. 1-2; abstract only.

Cutlar et al. (2013) "Gene therapy: pursuing restoration of dermal adhesion in recessive dystrophic epidermolysis bullosa". *Experimental dermatology*, 23(1), pp. 1-6.

Ferrari et al. (2006) "Gene therapy in combination with tissue engineering to treat epidermolysis bullosa". *Expert opinion on biological therapy*, 6(4), pp. 367-378.

Titeux et al. (2010) "SIN retroviral vectors expressing COL7A1 under human promoters for ex vivo gene therapy of recessive dystrophic epidermolysis bullosa". *Molecular Therapy*, 18(8), pp. 1509-1518.

* cited by examiner

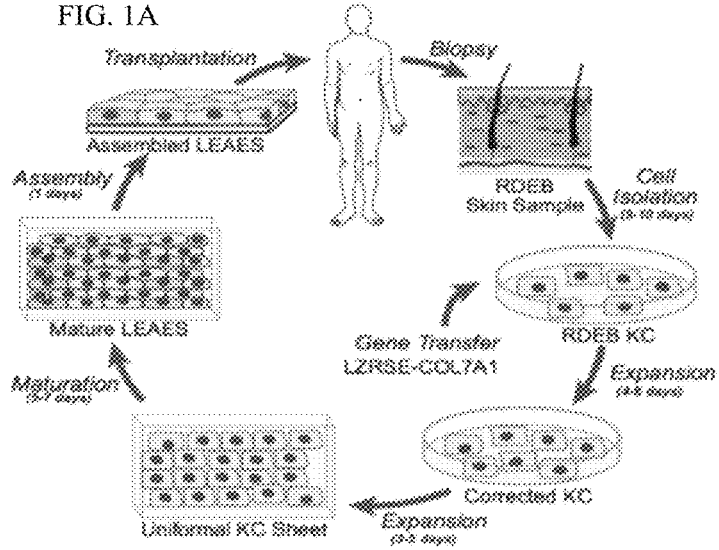
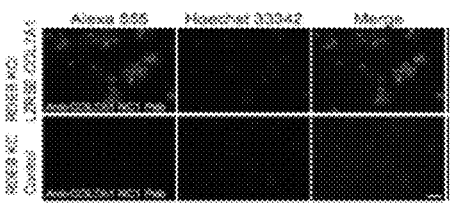
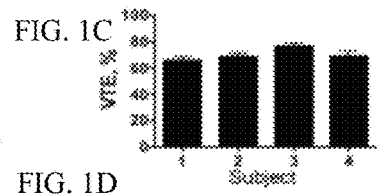
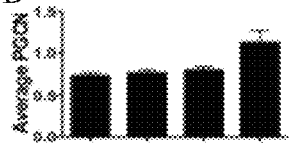
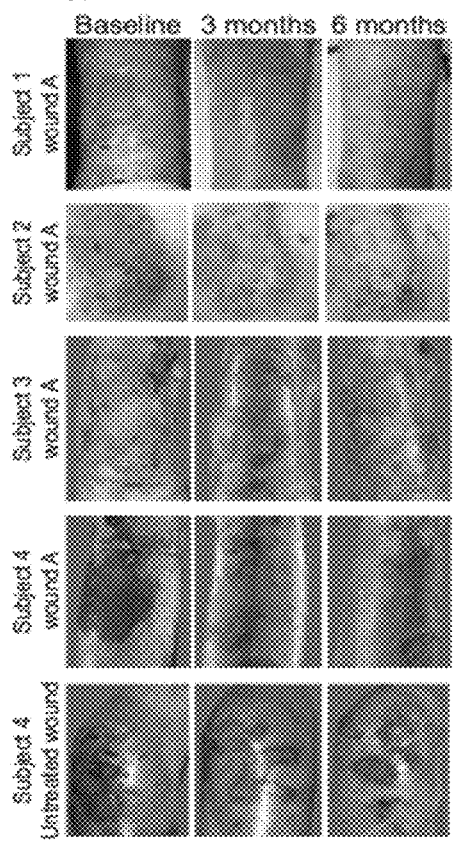
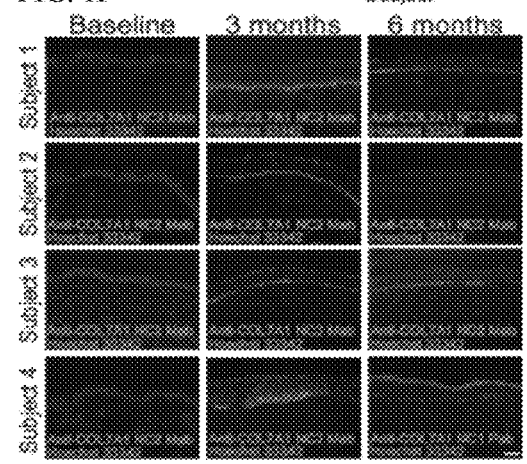
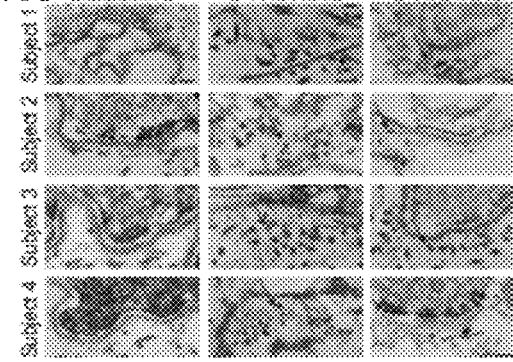

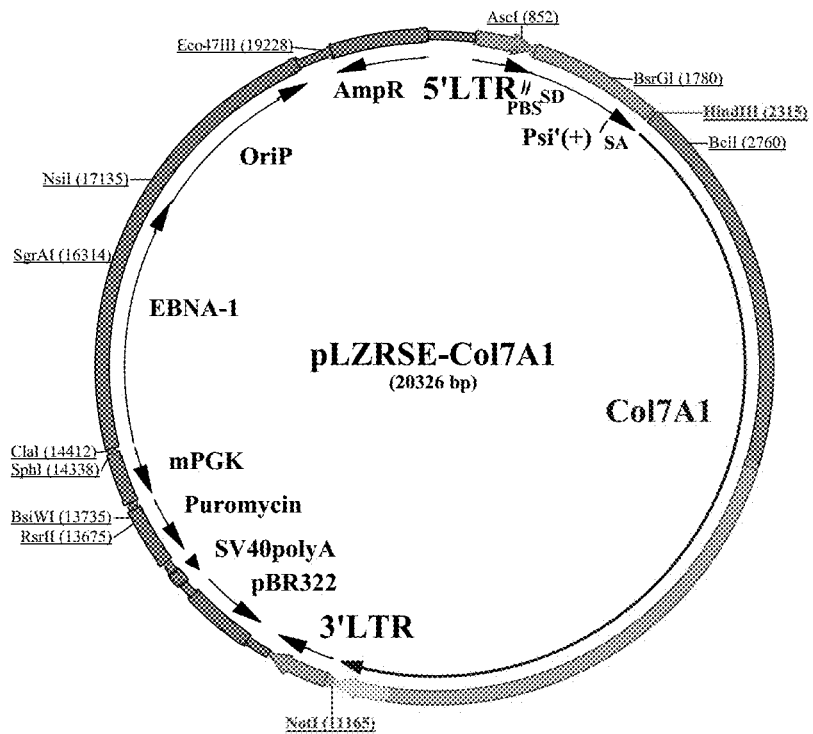

FIG. 13

Plasmid futures:

5'LTR (409-1000bp) – MoMuLV 5'LTR
Psi'(+)(1001-2287bp) – ORF reduced extended packaging signal Ψ⁺
PBS (1001-1018bp) – retrovirus primer binding site
SD (1058-1062bp) – splice donor
SA (1091-1093bp) – splice acceptor
Col7A1 (ORF 2325-11157bp) – Type VII collagen
3'LTR (11232-11849bp) – MoMuLV 3'LTR
pBR322 (12789-12088bp) – pBR322 *E.coli* origin of replication
SV40polyA (13075-12932bp) – SV40 polyadenylation signal
Puromycin (13797-13201bp) – puromycin resistance gene for selection in eukaryotes
mPGK (14383-13878bp) – mouse phosphoglycerol kinase-1 promoter
EBNA-1 (14432-17031BP) – Epstein-Barr virus nuclear antigen 1
OriP (17033-18962bp) – Epstein-Barr virus origin of replication
AmpR (20266-19310bp) - *bla* gene for ampicillin selection in prokaryotes

FIG. 14

| Subject | Site | Location | Description | Wound history | 1 month² | 3 months | 6 months |
|---|---|---|---|---|---|---|---|
| 1 | A | R distal forearm | Erosion | >5 yrs | | | |
| | B | L forearm | Erosion | >5 yrs | | | |
| | C | R proximal forearm | Erosion | >5 yrs | | | |
| | D | R shoulder | Inflamed erosion | >5 yrs | | | |
| | E | L arm | New blister | 1 wk | | | |
| | Z | R arm | Induced wound | New | | | |
| 2 | A | Central chest | Erosion | >5 yrs | | | |
| | B | L shoulder | Erosion and scar | >5 yrs | | | |
| | C | R forearm | Erosion and scar | 3-5 yrs | | | |
| | D | R posterior shoulder | Inflamed erosion | >5 yrs | | | |
| | E | Lower back | Erosion | >5 yrs | | | |
| | Z | R upper chest | Induced wound | New | | | |

FIG. 14 (Cont. 1)

| | | | | | | | | |
|---|---|---|---|---|---|---|---|---|
| 3 | A | R lateral hand | Erosion | 3-5 yrs | ▨ | ▨ | ▨ |
| | B | R medial hand | Scar tissue | 3-5 yrs | ▨ | ▨ | ▨ |
| | C | L ventral foot | Erosion and scar | 3-5 yrs | ▨ | ▨ | ▨ |
| | D | L hand | Scar tissue | 3-5 yrs | ▨ | ▨ | ▨ |
| | E | R foot | Erosion and scar | 3-5 yrs | ▨ | ▨ | ▨ |
| | Z | L ventral foot | Induced wound | New | ≡ | ≡ | ∴ |
| 4 | A | L distal forearm | Inflamed erosion | >5 yrs | ▨ | ▨ | ▨ |
| | B | L medial forearm | Inflamed erosion | >5 yrs | ≡ | ▨ | ≡ |
| | C | L proximal forearm | Inflamed erosion | >5 yrs | ▨ | ≡ | ≡ |
| | D | R lateral forearm | Inflamed erosion | >5 yrs | ▨ | ▨ | ▨ |
| | E | R distal forearm | Inflamed erosion | >5 yrs | ▨ | ▨ | ≡ |
| | Z | R medial forearm | Induced wound | New | ▨ | ▨ | ▨ |

# GENE THERAPY FOR RECESSIVE DYSTROPHIC EPIDERMOLYSIS BULLOSA USING GENETICALLY CORRECTED AUTOLOGOUS KERATINOCYTES

CROSS-REFERENCE

This application is a divisional of U.S. application Ser. No. 16/066,253 filed on Jun. 26, 2018, which is a 371 application and claims the benefit of PCT Application No. PCT/US2017/012061, filed Jan. 3, 2017, which claims benefit of U.S. Provisional Patent Application No. 62/274,700, filed Jan. 4, 2016; and U.S. Provisional Patent Application No. 62/414,533, filed Oct. 28, 2016, which applications are incorporated herein by reference in their entirety.

FEDERALLY SPONSORED RESEARCH AND DEVELOPMENT

This invention was made with Government support under contract AR055914 awarded by the National Institutes of Health. The Government has certain rights in the invention.

INCORPORATION BY REFERENCE OF SEQUENCE LISTING PROVIDED AS A SEQUENCE LISTING XML FILE

A Sequence Listing is provided herewith as a Sequence Listing XML, STAN-1295 DIV2_SEQ_LIST, created on Oct. 31, 2024, and having a size of 22,376 bytes. The contents of the Sequence Listing XML are incorporated herein by reference in their entirety.

FIELD

The present disclosure generally relates to methods and compositions to treat Epidermolysis Bullosa (EB) and corneal erosion.

BACKGROUND

Recessive Dystrophic Epidermolysis Bullosa (RDEB) is an inherited genetic blistering skin disorder caused by mutations in the COL7A1 gene (collagen VII, C7) leading to lack of C7 function. Patients with this disorder are characterized by widespread blistering and erosions of the skin and mucosal tissues, including oropharynx, conjunctiva, esophagus, as well as distal aspects of the genitourinary and gastrointestinal tract. Painful blistering and erosions are a major disability; however, scarring from healed wounds also causes significant morbidity, including mitten hand deformities (pseudosyndactyly), symblepharon of the eyes, esophageal strictures, microstomia, ankyloglossia, and strictures of the limbs. It is known that chronic wounding and scarring predisposes to invasive squamous cell carcinoma invasion, and this is a serious problem in RDEB, with invasive squamous cell carcinoma being the leading cause of death in this population starting from the second decade. Therefore, an optimal therapy for this disease would be one which could be implemented early to prevent disabling scarring from occurring, as well as preventing blistering. Also, the ability to systemically correct both skin and mucosal tissues would be highly desirable in an RDEB therapeutic approach.

Type VII collagen (C7) is a large homotrimeric triple helical collagenous molecule, which undergoes anti-parallel dimer formation at its NC2 end, followed by supramolecular assembly into attachment structures termed anchoring fibrils, which connect the lamina densa of the basement membrane zone (BMZ) to the papillary dermis. C7 contains a large NC1 domain, which binds laminin-332 in the lamina densa and a collagenous domain, which wraps around interstitial collagen fibrils in the papillary dermis. Thus, lack of C7 in RDEB produces blistering between the papillary dermis and lamina densa.

Despite advances in the molecular diagnosis of this disease, current therapy is limited to palliative care. While several approaches have been proposed to replace C7, all have their limitations. Topically applied, rC7 cannot penetrate intact skin and is limited to wounded areas. Intradermal rC7 protein injections for RDEB patients are another alternative; however, limited diffusion from conventional needle injection necessitates rC7 microneedle array delivery, which is not yet available for clinical use.

For therapeutic purposes, local delivery of C7 to the skin is desirable. The present invention addresses this issue. Systemic therapy of C7 may cause systemic toxicity. (See Hou et al. (2015), *Journal of Investigative Dermatology* 135, 3060-3067.)

SUMMARY

Compositions and methods are provided for the treatment of Epidermolysis Bullosa (EB) in a human subject. In the treatment methods of the invention, a population of human keratinocytes is engineered to express C7 by integrating a genetic construct encoding wild-type human C7. In some embodiments the level of expression is greater than normal human keratinocyte levels of expression. In some embodiments, the level of expression is smaller, similar, or same with normal human keratinocyte levels of expression. Included in the invention is an isolated population of keratinocytes engineered by the methods of the invention to express wild-type C7, which may be provided in a pharmaceutical unit dose composition. In some embodiments, the subject is a human suffering from a genetic defect in C7 causing the Epidermolysis Bullosa (EB). In the embodiments, the genetic defect is RDEB.

In some embodiments, the keratinocytes utilized in treatment are autologous keratinocytes. Methods of ex vivo engineering may be selected from, without limitation, virus-driven, including, but not limited to, retrovirus (e.g., gammaretrovirus), AAV virus, and lentivirus, or virus-free integrative methods, which include non-viral vectors, transposons, mini-circle integration, CRISPR/Cas9 genome editing system, and the like. In some embodiments, the gammaretrovirus comprises, consists essentially of, or yet further consists of, murine leukemia virus (MLV or MuLV), feline leukemia virus (FeLV), gibbon ape leukemia virus (GALV), and xenotropic murine leukemia virus-related virus (XMRV). In some embodiments, the non-viral vectors comprise, consist essentially of, or yet further consist of episomal vectors or integrating vectors with capacity of the genome editing features. In some embodiments, GMP-grade GalV-pseudotyped LZRSE-COL7A1 virus containing a functional COL7A1 cDNA under control of the MLV LTR is used to integrate the C7 gene into the keratinocytes. In some embodiments, the functional COL7A1 cDNA is a full-length wild-type human COL7A1 cDNA. In one embodiment, the functional COL7A1 cDNA include a genetic modification from the full-length wild-type human COL7A1 cDNA. In some embodiments, viral transduction is performed by overlaying viral supernatant over cell culture. In some embodiments, the keratinocytes thus treated meet pre-release criteria of virus transduction efficiency (VTE) >50% and proviral genome copy number (PGCN)≤3. In some embodiments, the PGCN is more than 3, 10, 20, 40, or 60. In some embodiment, the PGCN is less than 2, 1.5, 1, or 0.5.

In some embodiment, the endogenous mutated, dysfunctional, or truncated C7 gene is replaced, using a CRISPR/Cas system (or vector encoding said CRIPSR/Cas system) as described herein and a "donor" sequence (e.g., a functional COL7A1 cDNA or C7 gene) that is inserted into the gene following targeted cleavage.

In some embodiments of the invention, a method is provided for treatment of EB, the method comprising, consisting essentially of, or yet further consisting of, obtaining a population of keratinocytes from a subject suffering from EB, modifying the keratinocytes by retroviral transduction to express wild-type human C7, and reintroducing the keratinocytes into the individual. In some embodiments, keratinocytes are obtained from skin punch biopsies, which are cultured in vitro in keratinocyte media with or without serum. In some embodiments, the keratinocytes are cultured in a media with or without the feeder layer of cells. The epidermis is separated from the dermal layer and keratinocytes are obtained from the epidermal layer. At least about $10^6$ cells, at least about $2\times10^6$, and/or at least $4\times10^6$ cells are used for transduction to provide a population of genetically corrected cells. The cells are cultured to generate a sheet of from about 25 cm² to about 100 cm² for grafting. The genetically corrected keratinocyte sheets are placed on uninfected, eroded, and/or scarred wound sites that lacked clinical evidence of squamous cell carcinoma (SCC). Wound sites may be from about 50 cm², from about 100 cm², and/or from about 200 cm². In some embodiments, wounds are generated for grafts. In some such embodiments, the wound is electrocauterized to ablate residual non-corrected wound bed keratinocytes. Grafts are affixed to wound beds via dissolvable sutures following wound bed preparation.

In another embodiment, the disclosure provides a composition comprising, consisting essentially of, or yet further consisting of a population of keratinocytes genetically corrected to express wild-type human C7 at a dose effective to reduce the symptoms of EB, and a pharmaceutically acceptable carrier. In one aspect of the disclosure, the composition is frozen. In some embodiments, the keratinocytes are autologous relative to an individual selected for treatment.

In another embodiment, the disclosure provides a pharmaceutical composition comprising, consisting essentially of, or yet further consisting of a keratinocyte sheet, which comprises, consists essentially of, or yet further consists of skin cells ex vivo integrated with a genetic construct encoding a functional COL7A1 protein. In some embodiments, the keratinocyte sheet is placed on a bioengineered skin equivalent. In some embodiments, the keratinocyte sheet is placed on an acellular matrix, a collagen matrix, an ECM protein or chemical layer, or a biocompatible mesh. In one embodiment, the acellular matrix is made of human and/or animal dermis. In some embodiments, the biocompatible mesh is made of thermoplastic resin, polyethylene, ultra-high molecular weight polyethylene, high molecular weight polyolefin, uncoated monofilament polypropylene, polyether ether ketone, polyethylene terephthalate, polytetrafluoroethylene, expanded polytetrafluoroethylene, nylon, silicon, or any combination thereof.

It is shown herein, autologous RDEB keratinocytes were isolated from skin biopsies and transduced with retrovirus carrying functional (e.g., full-length) human COL7A1. For each subject, autologous epidermal sheets (~35 cm²) were manufactured and grafted onto prepared wound beds. Endpoints included safety, efficacy as a percent of wound healing compared with baseline, and evidence of C7 expression at 3 and 6 months post transplantation. All grafts were well tolerated by all subjects, and no serious adverse events were reported (systemic viral infection, auto-immunity, skin cancer occurrence within grafts). At 3-6 months, a majority of the grafts showed 75% healing. Biopsies from graft sites showed robust C7 expression at the dermal-epidermal junction at 3 months, and at 6 months the presence of normal anchoring fibrils. COL7A1 ex-vivo gene transfer had a favorable safety profile and displayed encouraging efficacy in subjects with inherited RDEB.

BRIEF DESCRIPTION OF THE DRAWINGS

FIG. 1A-1G. (FIG. 1A) RDEB genetic correction flow chart. KC—epidermal keratinocytes, LEAES—LZRSE-COL7A1 engineered autologous epidermal sheet grafts. (FIG. 1B) Indirect immunofluorescence (IIF) of LZRSE-COL7A1 virus transduced RDEB KC. Anti-type VII collagen polyclonal antibody (orange); Hoechst 33342 nuclei (blue). Scale bar, 100 μm. (FIG. 1C) Quantification of the virus transduction efficiency (VTE) in corrected KC of 4 RDEB subjects. (FIG. 1D) Quantification of an average proviral copy number (PGCN) in corrected KC of 4 RDEB subjects. (FIG. 1E) Clinical representation of RDEB phenotype before and post graft transplantation. Note blisters prior to corrected skin transplantation and in untreated wounds, compare to 3 and 6 months post LEAES grafting. (FIG. 1F) IIF analyses of type VII collagen expression in skin grafts. Anti-type VII collagen NC2 Mab LH24 and NC1 Pab FNC1 (green); Hoechst 33342 nuclei (blue); Note linear green staining of type VII collagen at the dermal-epidermal junction of the corrected tissue grafts. Scale bar, 100 μm. (FIG. 1G) Immuno-EM analyses of a corrected RDEB skin grafts. Tissue sections were labeled en bloc with anti-type VII collagen NC2 Mab LH24, followed by anti-mouse IgM-conjugated immunogold particles (black dots, indicated by arrows). Scale bar, 200 nm.

(FIG. 5A) Clinical representation of RDEB phenotype before and post graft transplantation. (FIG. 5B) IIF analyses of type VII collagen expression in skin grafts. Anti-type VII collagen NC2 Mab LH24 (green); Hoechst 33342 nuclei (blue); keratin 14 (anti-K14 Pab, orange); keratin 1 (anti-K1 Pab, orange) and loricrin (anti-loricrin Pab, orange). Note linear green staining of type VII collagen at the dermal-epidermal junction of the corrected tissue grafts at all time points. Scale bar, 100 μm.

(FIG. 6A) Clinical representation of RDEB phenotype before and post graft transplantation. (FIG. 6B) IIF analyses of type VII collagen expression in skin grafts. Anti-type VII collagen NC2 Mab LH24 (green); Hoechst 33342 nuclei (blue); keratin 14 (anti-K14 Pab, orange); keratin 1 (anti-K1 Pab, orange) and loricrin (anti-loricrin Pab, orange). Note linear green staining of type VII collagen at the dermal-epidermal junction of the corrected tissue grafts at 3 months. Scale bar, 100 μm.

(FIG. 7A) Clinical representation of RDEB phenotype before and post graft transplantation. (FIG. 7B) IIF analyses of type VII collagen expression in skin grafts. Anti-type VII collagen NC2 Mab LH24 (green); Hoechst 33342 nuclei (blue); keratin 14 (anti-K14 Pab, orange); keratin 1 (anti-K1 Pab, orange) and loricrin (anti-loricrin Pab, orange). Note linear green staining of type VII collagen at the dermal-epidermal junction of the corrected tissue grafts at all time points. Scale bar, 100 μm.

(FIG. 8A) Clinical representation of RDEB phenotype before and post graft transplantation. (FIG. 8B) IIF analyses of type VII collagen expression in skin grafts. Anti-type VII collagen NC2 Mab LH24 (green); Hoechst 33342 nuclei (blue); keratin 14 (anti-K14 Pab, orange); keratin 1 (anti-K1 Pab, orange) and loricrin (anti-loricrin Pab, orange). Note linear green staining of type VII collagen at the dermal-epidermal junction of the corrected tissue grafts at 3 months with LH24 Mab and 6 months with NC1 Pab. Scale bar, 100 μm.

(FIG. 11A) Western blot analysis showing cross-reactivity of subject 4 serum to the full-length C7 prior and post graft transplantation (3 months). (FIG. 11B) Subject 4 serum obtained pre- and 3 months post grafting is specific to the enzymatically (pepsin) digested C7 protein containing NC2 domain. Control (right lane) confirms NC2 domain presence in the digested C7 fraction using NC2 specific Pab (NC2-10) 5.

FIG. 13. depicts the map of the pLZRSE-COL7A1 retroviral plasmid.

FIG. 14. Graft Site Baseline Characteristics, Clinical Response and Skin Biopsy Follow-Up Results. Diagonal line indicates graft is ≥75% healed, Horizontal line indicates 50-74% healed, dots indicate <49% healed based on clinical and photographic assessment by investigators at 2±3 weeks.

DETAILED DESCRIPTION

Figure 2:
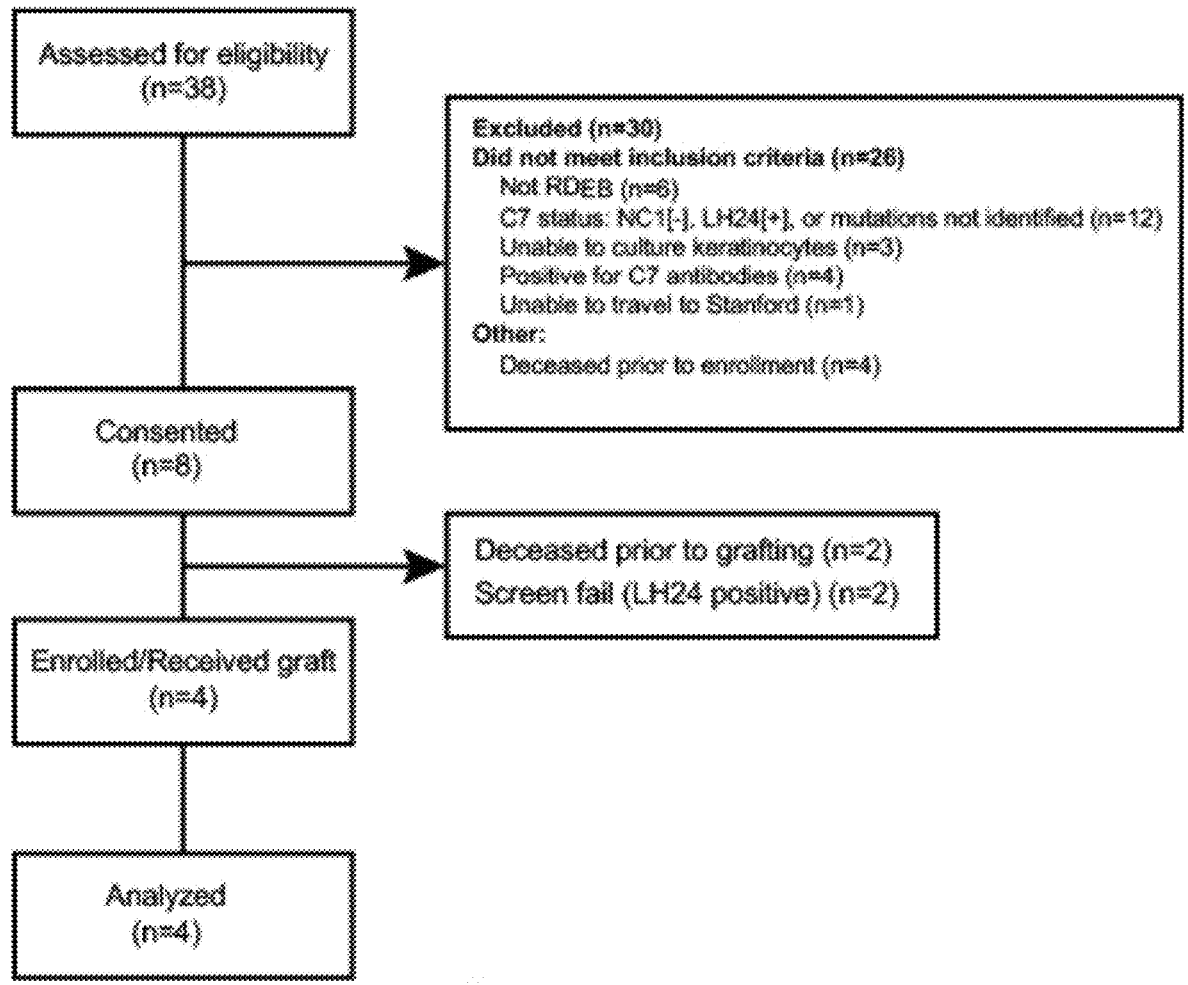
FIG. 2. CONSORT diagram of subject enrolment in Phase I trial.

It is to be understood that this invention is not limited to the particular methodology, protocols, cell lines, animal species or genera, and reagents described, as such may vary. It is also to be understood that the terminology used herein is for the purpose of describing particular embodiments only and is not intended to limit the scope of the present invention, which will be limited only by the appended claims.

As used herein, the singular forms "a," "an," and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Any embodiment of any of the present methods, devices, and systems may consist of, or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only, or the alternatives are mutually exclusive, although the disclosure supports a definition that refers to only alternatives and "and/or."

Throughout this application, the term "about" is used to indicate that a value includes the standard deviation of error for the device or method being employed to determine the value.

Conditions of interest for treatment with engineered keratinocytes of the present invention include, without limitation, various forms of Epidermolysis Bullosa, including acquired and congenital forms, the latter of which may be recessive or dominant.

Based on the recent classification system, Dystrophic Epidermolysis Bullosa (DEB) includes three subtypes: recessive DEB, severe generalized (RDEB-sev gen) (formerly called Hallopeau-Siemens type (RDEB-HS); recessive DEB, generalized other (RDEB-O) (formerly called non-Hallopeau-Siemens type (RDEB-non-HS); and dominant DEB (DDEB). In RDEB-sev gen, blisters affecting the whole body may be present in the neonatal period. Oral involvement may lead to mouth blistering, fusion of the tongue to the floor of the mouth, and progressive diminution of the size of the oral cavity. Esophageal erosions can lead to webs and strictures that can cause severe dysphagia. Consequently, severe nutritional deficiency and secondary problems are common. Corneal erosions can lead to scarring and loss of vision. Blistering of the hands and feet followed by scarring fuses the digits into "mitten" hands and feet, a hallmark of this disorder. The lifetime risk of aggressive squamous cell carcinoma is over 90%. In DDEB, blistering is often mild and limited to hands, feet, knees, and elbows, but nonetheless heals with scarring. Dystrophic nails, especially toenails, are common and may be the only manifestation of DDEB.

Conventional treatment of manifestations is primarily supportive, including wound dressing and nutritional support. Occupational therapy may help prevent hand contractures. Surgical release of fingers often needs to be repeated. Keratinocytes engineered to express wild-type C7 can find use in therapy for Dystrophic Epidermolysis Bullosa.

In addition to inherited forms of EB, the acquired form of Epidermolysis Bullosa (EBA) involves pathology in type VII collagen and may be treated with the engineered keratinocytes of the disclosure. Circulating autoantibodies in patients with EBA recognize epitopes in type VII collagen molecules, and molecular cloning of the type VII collagen cDNAs have provided the tools to identify the predominant immunoepitopes within the amino-terminal NC-1 domain of type VII collagen. The antigenic properties of the NC-1(VII) domain are further highlighted by the fact that monoclonal antibodies, such as H3A and L3D, which are in clinical use to map type VII collagen in the skin of patients with inherited forms of EB, also identify epitopes in this portion of the protein. In addition to circulating autoantibodies recognizing type VII collagen epitopes in EBA, bullous lesions in some patients with systemic lupus erythematosus have also been associated with anti-type VII collagen antibodies.

Collagen. As used herein the term "collagen" refers to compositions in which at least about 50%, at least about 60%, at least about 70%, at least about 80%, at least about 90%, at least about 95%, or more of the protein present is collagen in a triple helical configuration. The folding of the individual α-chains into the triple-helical conformation is predicated upon the characteristic primary sequence, including repeating Gly-X-Y triplet sequences. Collagens are widely found in vertebrate species and have been sequenced for many different species. Due to the high degree of sequence similarity between species, collagen from different species can be used for biomedical purposes, e.g., between mammalian species, although the human protein may be preferred.

FACIT collagens (fibril-associated collagens with interrupted triple helices) include types IX, XII, XIV, XIX, XX, and XXI. Several of the latter types of collagens associate with larger collagen fibers and serve as molecular bridges, stabilizing the organization of the extracellular matrix. Collagen VII, (COL7A1, Chromosome 3, NC_000003.10 (48576510 . . . 48607689, complement)) is of particular interest. Type VII collagen is a major component of anchoring fibrils.

Type VII collagen is a long, 424 nm, triple-helical domain with flanking non-collagenous sequences. Type VII collagen molecules include a central collagenous, triple-helical segment flanked by the non-collagenous NC-1 and NC-2 domains. Unlike interstitial collagens, the repeating Gly-X-Y sequence is interrupted by 19 imperfections due to insertions or deletions of amino acids in the Gly-X-Y repeat sequence. Most notably, in the middle of the triple-helical domain, there is a 39-amino acid non-collagenous "hinge" region which is susceptible to proteolytic digestion with pepsin. The amino-terminal NC-1 domain of type VII, approximately 145 kDa in size, includes sub-modules with homology to known adhesive proteins, including segments with homology to cartilage matrix protein (CMP), nine consecutive fibronectin type III-like (FN-III) domains, a segment with homology to the A domain of von Willebrand factor, and a short cysteine and proline-rich region. The carboxy-terminal non-collagenous domain, NC-2, is relatively small, ~30 kDa, and it contains a segment with homology to Kunitz protease inhibitor molecule.

The human type VII collagen gene, COL7A1 has a complex structure with a total of 118 separate exons. The gene is, however, relatively compact, and most of the introns are relatively small; consequently, the size of the entire human COL7A1 gene is only ~32 kb, encoding a messenger RNA of ~8.9 kb. COL7A1 has been mapped to the short-arm of human chromosome 3, region 3p21.1. The type VII collagen gene structure and the encoded primary sequence of the protein are well conserved, and for example, the mouse gene shows 84.7% homology at the nucleotide and 90.4% identity at the protein level.

Type VII collagen is synthesized both by epidermal keratinocytes and dermal fibroblasts in culture. Upon synthesis of complete pro-α1(VII) polypeptides, three polypeptides associate through their carboxy-terminal ends to a trimer molecule which in its collagenous portion folds into the triple-helical formation. The triple-helical molecules are then secreted to the extracellular milieu where two types of VII collagen molecules align into an anti-parallel dimer with the amino-terminal domains present at both ends of the molecule. This dimer assembly is accompanied by proteolytic removal of a portion of the carboxy-terminal end of both type VII collagen molecules and stabilization by intermolecular disulfide bond formation. Subsequently, a large number of these anti-parallel dimers aggregate laterally to form anchoring fibrils.

Glycine substitution mutations in the triple helical domain of COL7A1 (especially in exons 73, 74, and 75) predominate in Dominant Dystrophic Epidermolysis Bullosa (DDEB). Mutations p.Gly2034Arg and p.Gly2043Arg are the most common DDEB-causing mutations, making up 50% of the dominant mutations reported in the largest US cohort. Glycine substitutions as well as other amino acid substitutions and splice junction mutations outside of this region may also be found in dominant DEB.

More than 400 recessive DEB-causing mutations spanning the entire gene have been described for all forms of DEB. Each mutation, however, accounts for no more than 1%-2% of the total number of mutations. Null mutations predominate in RDEB, though glycine substitutions and other amino acid substitutions have been described. Milder forms of RDEB are often caused by splice junction mutations or other missense mutations.

A "native sequence" polypeptide is one that has the same amino acid sequence as a polypeptide derived from nature. Such native sequence polypeptides can be produced by recombinant means according to the methods set forth herein. Thus, a native sequence polypeptide can have the amino acid sequence of, e.g., naturally occurring human polypeptide, murine polypeptide, or polypeptide from any other mammalian species, and the like. The term "native sequence collagen VII protein" includes the native proteins with or without the initiating N-terminal methionine (Met).

A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active collagen VII variant will have an amino acid sequence having at least about 90% amino acid sequence identity with a native sequence collagen VII polypeptide, preferably at least about 95%, more preferably at least about 99%.

A "functional derivative" of a native sequence collagen, VII polypeptide is a compound having a qualitative biological property in common with a native sequence collagen VII polypeptide. "Functional derivatives" include, but are not limited to, fragments of a native sequence and derivatives of a native sequence collagen VII polypeptide and its fragments, provided that they have a biological activity in common with a corresponding native sequence collagen VII polypeptide. The term "derivative" encompasses both amino acid sequence variants of collagen VII polypeptide and covalent modifications thereof.

The term "wound bed" refers to the uppermost viable layer of wound. In one embodiment, the wound bed is covered by slough or eschar. In another embodiment, the wound bed can be assessed for presence of granulation tissue fibrin slough, eschar, bone, tendon, and/or other underlying structures.

The term "virus transduction efficiency (VTE) test" is a test to measure the ratio of the number of viral transduced cells to the total cells subject to the transduction. In one embodiment, the VTE is measured by immunofluorescent staining with antibody targeting a protein expressed on the transduced virus. In another embodiment, the VTE is measured by real-time PCR or quantitative PCR.

The term "proviral genome copy number" or "PGCN" refers to the number of proviral DNA copies in the virally transduced cells. Thus, the PGCN test measures the copy number of proviral DNA in a cell after viral transduction or infection. In one embodiment, the copy number is measured by real-time PCR or quantitative PCR. In another embodiment, PGCN is measured by southern blot or a high-throughput method. In some embodiment, the PGCN is less than 3, 2, 1, 0.5. In some embodiment, the PGCN is more than 3, 10, 100, or 1,000.

The term "sterility test" refers to a test which attempts to reveal the presence or absence of viable contaminating micro-organisms in a sample, and is often used to eliminate false positive results. In one embodiment, the false positive results are generated due to contamination from the environment or errors.

The term "endotoxin" refers to a toxin associated with the outer membranes of certain gram-negative bacteria, including, but not limited to, *Brucella, Neisseria*, and *Vibrio* species. In one embodiment, the endotoxins are not secreted but are released only when the cells are disrupted. The endotoxin can be measured or tested by a gel-clot method, a chromogenic method, a turbidimetric method, or combination thereof.

The term "mycoplasma" refers to a population of bacteria that lack a cell wall around their cell membrane such that the bacteria are less affected or unaffected by certain types of antibiotics. The mycoplasma test includes, but is not limited to, Agar-and-broth procedure, DNA detection, Enzymatic and ELISA methods, and PCR.

The term "gram stain sterility test" refers to a procedure for detecting bacteria and/or fungi in the sample. In one embodiment, the gram stain sterility test can show the presence or absence of bacteria or fungi in the sample, and/or their general types.

The term "viability test" refers to a test to determine the ability of organs, cells or tissues to maintain or recover viability, which includes, but is not limited to, mechanical activity, motility, contraction, mitotic activity of the organs, cells, or tissues. In one embodiment, the LZRSE-COL7A1 Engineered Autologous Epidermal Sheets (LEAES) viability test is to test the ability of cells or tissues on LEAES to maintain or recover viability.

The term "replication competent retrovirus (RCR)," in this disclosure, refers to the retrovirus that is capable of replication, even though the retroviral vectors are designed to be replication defective. In one embodiment, the RCR is generated during manufacturing through homologous or non-homologous recombination between the transfer vector, packaging components and endogenous retroviral elements in producer cells. An RCR test is to detect the RCR in a sample.

The term "cytotoxic T cell assay" refers to an assay for evaluating cell-mediated immune functions.

The term "post-release test," in this disclosure, refers to one or more tests after the epidermal sheet is released from the plate, including, but not limited to, sterility test, RCR test, mycoplasma test, viability test, and gram stain sterility test.

The term "genetic modification" refers to a process of altering a gene of an organism or inserting a gene from one organism into another organism. In one embodiment, the genetic modification comprises, consists essentially of, or yet consists of insertion, deletion, and/or mutation. The term "insertion" means addition of one or more nucleotide base pairs into a nucleotide sequence. The term "deletion" refers to a part of a chromosome or a nucleotide sequence that is removed or missing. The term "mutation" is alteration of nucleotide sequence (e.g., DNA sequence). The mutation can occur in various sizes, including, but not limited to, a single base pair (i.e., point mutation), several base pairs, or up to a large segment of chromosome.

The term "conservative genetic modification" refers to genetic modification that maintain same or similar biochemical properties of a polypeptide encoded by the genetically modified gene. For example, both aspartic acid and glutamic acid are both small, negatively charged residues. In some embodiment, it is a conservative genetic modification by mutate aspartic acid to glutamic acid in a polypeptide.

Prolyl 4-hydroxylase (P4HA; EC 1.14.11.2) plays a central role in collagen synthesis. It catalyzes the formation of 4-hydroxyproline in collagens by hydroxylation of proline residues in peptide linkages. The 4-hydroxyproline residues are essential for the folding of the newly synthesized procollagen polypeptide chain into triple helical molecules. The active enzyme is a tetramer of 2 alpha and 2 beta subunits with a molecular weight of about 240,000. The beta subunit (P4HB) is identical to the enzyme disulfide isomerase (EC 5.3.4.1) and a major cellular thyroid-binding protein. The alpha subunit contributes to a major part of the catalytic site of the enzyme. The polypeptide is 517 amino acid residues and a signal peptide of 17 amino acids.

The P4HA gene covers more than 69 kilobases and consists of 16 exons. Evidence had previously been presented for a mutually exclusive alternative splicing of RNA transcripts of the gene. The present data indicated that the mutually exclusive sequences found in the mRNAs are coded by 2 consecutive, homologous 71-bp exons, 9 and 10. These exons are identical in their first 5 base pairs and the overall identity between them is 61% at the nucleotide level and 58% at the level of the coded amino acids. Both types of mRNA were found to be expressed in all of the tissues studied, but in some tissues the type coding for the exon 9 or exon 10 sequences was more abundant than the other type.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

In the present methods, collagen VII is produced by introducing into a cell population on an integrating, usually viral expression construct. The DNA encoding collagen VII polypeptide may be obtained from any cDNA library prepared from tissue expressing the collagen VII polypeptide mRNA, prepared from various sources. The collagen VII polypeptide-encoding gene may also be obtained from a genomic library or by oligonucleotide synthesis. An alternative means to isolate the gene encoding is to use PCR methodology.

The nucleic acid (e.g., cDNA or genomic DNA) encoding the collagen VII polypeptide is inserted into a construct for expression, operably linked to elements required for expression. Many such constructs are available. The components generally include, but are not limited to, one or more of the following: the coding sequence, one or more marker genes, an enhancer element, a promoter, and a transcription termination sequence.

A "vector" is capable of transferring nucleic acid sequences to target cells. For example, a vector may comprise a coding sequence capable of being expressed in a target cell. For the purposes of the present invention, "vector construct," "expression vector," and "gene transfer vector," generally refer to any nucleic acid construct capable of directing the expression of a gene of interest and which is useful in transferring the gene of interest into target cells. Thus, the term includes cloning and expression vehicles, as well as integrating vectors.

An "expression cassette" comprises any nucleic acid construct capable of directing the expression of any RNA transcript including gene/coding sequence of interest as well as non-translated RNAs, such as shRNAs, microRNAs, siRNAs, anti-sense RNAs, and the like. Such cassettes can be constructed into a "vector," "vector construct," "expression vector," or "gene transfer vector," in order to transfer the expression cassette into target cells. Thus, the term includes cloning and expression vehicles, as well as viral vectors.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adapters or linkers are used in accordance with conventional practice.

Expression vectors will contain a promoter that is recognized by the autologous leukocyte, or a host cell for expression of mRNAs, and is operably linked to the collagen VII coding sequence. Promoters are untranslated sequences located upstream (5') to the start codon of a structural gene (generally within about 100 bp to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well-known. Heterologous promoters are preferred, as they generally permit greater transcription and higher yields.

Transcription from vectors in mammalian host cells may be controlled, for example, by promoters obtained from the genomes of viruses such as polyomavirus, fowlpox virus, adenovirus (such as adenovirus 2), bovine papilloma virus, avian sarcoma virus, cytomegalovirus, a retrovirus, hepatitis-B, simian virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment.

Transcription by higher eukaryotes is often increased by inserting an enhancer sequence into the vector. Enhancers are cis-acting elements of DNA, usually about from 10 bp to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter.

Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA.

Vectors and systems for integration of an expression cassette into a cell are known in the art, and may include, without limitation, retroviral vectors. Many vectors useful for transferring exogenous genes into target mammalian cells are available. Retrovirus-based vectors have been shown to be particularly useful. Combinations of retroviruses and an appropriate packaging line may be used, where the capsid proteins will be functional for infecting the target cells. Usually, the cells and virus are incubated for at least about 24 hours in the culture medium. The cells are then allowed to grow in the culture medium for short intervals in some applications, e.g., 24-73 hours, or for at least two weeks, and may be allowed to grow for five weeks or more, before analysis. Commonly used retroviral vectors are "defective," i.e., unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic, and xenotropic. Retroviruses bearing amphotropic envelope protein, e.g., 4070A (Danos et al, supra.), are capable of infecting most mammalian cell types, including human, dog, and mouse. Amphotropic packaging cell lines include PA12 (Miller et al. (1985) Mol. Cell. Biol. 5:431B437); PA317 (Miller et al. (1986) Mol. Cell. Biol. 6:2895B2902); GRIP (Danos et al. (1988) PNAS 85 6460B6464). Retroviruses packaged with xenotropic envelope protein, e.g., AKR env, are capable of infecting most mammalian cell types, except murine cells.

The sequences at the 5' and 3' termini of the retrovirus are long terminal repeats (LTR). A number of LTR sequences are known in the art and may be used, including the MMLV-LTR; HIV-LTR; AKR-LTR; FIV-LTR; ALV-LTR; etc. The 5' LTR acts as a strong promoter, driving transcription of the introduced gene after integration into a target cell genome.

Keratinocytes. Freshly collected primary keratinocytes may be collected, isolated from a skin punch biopsy, and transduced following a period of culture to isolate the keratinocytes from dermal cells. In vitro-expanded epithelial keratinocytes can form a sheet. In some embodiments, the transduced cells are administered to the patient within about 1 to 100 days, 1 to 50 days, 1 to 20 days, 1 to 10 days, 1 to 5 days, 1 to 3 days, 1 to 2 days, or 1 day from the time the cells were transduced.

Any of a variety of culture media may be used in the present methods as would be known to the skilled person (see e.g., Current Protocols in Cell Culture, 2000-2009 by John Wiley & Sons, Inc.). Illustrative media also includes, but is not limited to, keratinocyte medium, which may be serum-free, and may contain appropriate keratinocyte supplements.

The disclosure provides a method for treating Epidermolysis Bullosa (EB) in a subject, the method comprising, alternatively consisting essentially of, or yet further consisting of obtaining the subject a population of skin cells; correcting the skin cells ex vivo by integration of a genetic construct encoding functional (e.g., full-length wild-type) human collagen VII (COL7A1) protein; culturing the genetically corrected cells to form a keratinocyte sheet; and transplanting a graft of the keratinocyte sheet to a skin wound bed. The disclosure also relates to use of a population of skin cells to treat Epidermolysis Bullosa (EB) in a subject, wherein the population of skin cells is corrected by transduction with a virus comprising a genetic construct encoding a full-length wild-type human collagen VII (COL7A1) protein to obtain a population of transduced skin cells having a proviral genome copy number (PGCN) and wherein the PGCN of the transduced population of skin cells is no more than 3. In some embodiments, the genetically corrected cells are cultured in a DFF31 medium comprising, alternatively consisting essentially of, or yet further consisting of Dulbecco's Modified Eagle Medium and F12 medium. In one embodiment, the skin cells are corrected by transduction with a virus comprising, alternatively consisting essentially of, or yet further consists of the expression construct, wherein the virus comprises, alternatively consists essentially of, or yet further consists of retrovirus, AAV (adeno-associated virus), or lentivirus. In another embodiment, the retrovirus is LZRSE-virus. In one embodiment, the retrovirus is GalV-pseudotyped. In a further embodiment, the keratinocytes thus transduced meet pre-release criteria of virus transduction efficiency (VTE)>50% and proviral genome copy number (PGCN)≤3. In some embodiments, the PGCN is less than 2.5, 2, 1.5, or 1. In another embodiment, the PGCN is between 3-20, 20-40, 40-60, 60-80, or 80-100. In another embodiment, the PGCN is more than 100. In some embodiments, the keratinocyte sheet differs in size. One of ordinary skill in the art can determine the size of the keratinocyte sheet.

In some embodiment, the endogenous mutated, dysfunctional, or truncated C7 gene is replaced, using a CRISPR/Cas system (or vector encoding said CRIPSR/Cas system) as described herein and a "donor" sequence (e.g., a functional COL7A1 cDNA or C7 gene or a full-length wide-type COL7A1 cDNA or gene) that is inserted into the gene following targeted cleavage. CRISPR/Cas systems are found in 40% of bacteria and 90% of archaea and differ in the complexities of their systems. See, e.g., U.S. Pat. No. 8,697,359, which is incorporated by reference in its entirety. The CRISPR loci (clustered regularly interspaced short palindromic repeat) is a region within the organism's genome where short segments of foreign DNA are integrated between short repeat palindromic sequences. These loci are transcribed and the RNA transcripts ("pre-crRNA") are processed into short CRISPR RNAs (crRNAs). There are three types of CRISPR/Cas systems which all incorporate these RNAs and proteins known as "Cas" proteins (CRISPR associated). Types I and III both have Cas endonucleases that process the pre-crRNAs, that, when fully processed into crRNAs, assemble a multi-Cas protein complex that is capable of cleaving nucleic acids that are complementary to the crRNA. CRISPR/Cas system that binds to target site in a region of interest in an endogenous gene (e.g., an endogenous or safe harbor gene, or a regulatory gene or its DNA target) in a genome, wherein the CRISPR/Cas system comprises one or more engineered single guide RNAs that recognize the target gene and a functional domain (e.g., a transcriptional regulatory domain and/or a nuclease domain). In some embodiment, the CRISPR/Cas system as described herein may bind to and/or cleave the region of interest (e.g., endogenous C7 gene from EB tissues) in a coding or non-coding region within or adjacent to the gene, such as, for example, a leader sequence, trailer sequence or intron, or within a non-transcribed region, either upstream or downstream of the coding region. In certain embodiments, the CRISPR/Cas binds to and/or cleaves a gene, e.g., the mutated, dysfunctional, or truncated C7 gene.

In one aspect, the wound is free of non-corrected wound bed keratinocytes. In one embodiment, the wound is treated to ablate non-corrected wound bed keratinocytes. In another aspect, the subject suffers from Recessive Dystrophic Epidermolysis Bullosa (RDEB). In a different aspect, the subject is human.

In another embodiment, the keratinocyte sheet is subject to one or more tests selected from a group consisting of VTE test, PGCN test, sterility test, endotoxin test, mycoplasma test, gram stain sterility test, LEAES viability test, post-release test, RCR test, cytotoxic T cell assay, anti-C7 LH24 mAb characterization, electron microscopy, Immuno-electron microscopy, immunofluorescence staining, C7 expression, and AF analysis. In one aspect, the immunofluorescence staining comprises, alternatively consists essentially of, or yet further consists of direct or indirect immunofluorescence staining.

In some embodiments, the keratinocyte sheet is placed on an acellular matrix, a collagen matrix, or a biocompatible mesh. In one embodiment, the biocompatible mesh is made of thermoplastic resin, polyethylene, ultra-high molecular weight polyethylene, high molecular weight polyolefin, uncoated monofilament polypropylene, polyether ether ketone, polyethylene terephthalate, polytetrafluoroethylene, expanded polytetrafluoroethylene, nylon, silicon, or any combination thereof.

In some embodiments, the skin cells comprise, alternatively consist essentially of, or yet further consist of keratinocytes. In one embodiment, the skin cells comprise, alternatively consist essentially of, or yet further consist of stem cells. In another embodiment, the method further comprises, alternatively consists essentially of, or yet further consists of differentiating the stem cells into keratinocytes. In one aspect, the stem cells are differentiated before, after or during transduction. In some embodiments, the stem cells are differentiated (e.g., into keratinocytes or corneal epithelial cells) before the transduction. In some embodiments, the stem cells are differentiated after the transduction. In a further embodiment, the stem cells are differentiated during the transduction.

Patients with RDEB can frequently develop debilitating painful corneal erosion. Thus, provided in the disclosure is also a method for treating corneal erosion in a subject, the method comprising, alternatively consisting essentially of, or yet further consisting of obtaining from the subject a population of corneal cells; correcting the corneal cells ex vivo by integration of a genetic construct encoding functional (e.g., full-length wild-type) human collagen VII (COL7A1) protein; culturing the genetically corrected cells to form a corneal cell sheet; and transplanting a graft of the corneal cell sheet to a corneal surface. In some aspect, the corneal cells comprise, alternatively consist essentially of, or yet further consist of corneal epithelial cells. In another aspect, the corneal cells comprise, alternatively consist essentially of, or yet further consist of stem cells. In some embodiment, the method further comprises, alternatively consists essentially of, or yet further consists of differentiating the stem cells into corneal epithelial cells.

In some aspect, the corneal cells are corrected by transduction with a virus comprising the genetic construct, wherein the virus comprises, alternatively consists essentially of, or yet further consists of retrovirus, lentivirus, or AAV. In one embodiment, the retrovirus is LZRSE-virus. In some embodiments, the retrovirus is GalV-pseudotyped. In some embodiments, the corneal cells thus transduced meet pre-release criteria of virus transduction efficiency (VTE) >50% and proviral genome copy number (PGCN)≤3. In some embodiments, the PGCN is less than 2.5, 2, 1.5, or 1. In another embodiment, the PGCN is between 3-20, 20-40, 40-60, 60-80, or 80-100. In another embodiment, the PGCN is more than 100. In some aspect, the subject suffers from Recessive Dystrophic Epidermolysis Bullosa (RDEB). In a different aspect, the subject is human.

In one aspect, the corneal cell sheet is subject to one or more tests selected from a group consisting of VTE test, PGCN test, sterility test, endotoxin test, mycoplasma test, gram stain sterility test, LEAES viability test, post-release test, RCR test, cytotoxic T cell assay, anti-C7 LH24 mAb characterization, electron microscopy, Immuno-electron microscopy, immunofluorescence staining, C7 expression, and AF analysis. In one embodiment, the immunofluorescence staining comprises, alternatively consists essentially of, or yet further consists of direct or indirect immunofluorescence staining. In some embodiments, the corneal cell sheet is placed on an acellular matrix, collagen matrix, or a biocompatible mesh.

In one aspect, the biocompatible mesh can be made from non-resorbable materials, including, but not limited to, biocompatible metals such as titanium alloys, stainless steel, cobalt-chromium alloys, and nickel-titanium alloys. In another aspect, the layer of biocompatible mesh can be made from non-resorbable polymeric materials, including, but not limited to, thermoplastic resins, polyethylenes, ultra-high molecular weight polyethylene, high molecular weight polyolefins, uncoated monofilament polypropylene, polyether ether ketone, polyethylene terephthalate, polytetrafluoroethylene, expanded polytetrafluoroethylene, nylon, any polymer or aliphatic hydrocarbons containing one or more double bonds, any other appropriate porous materials, or any other appropriate porous material that can be bent or otherwise formed into a shape.

In another aspect, the biocompatible mesh can be composed of a synthetic or biological resorbable polymeric material, including, but not limited to, polyglycolic acid, poly-L-lactic acid (PLLA), poly-D,L-lactic acid (PDLA), trimethylene carbonate (TMC), poly-£-caprolactone, poly-P-dioxanone, copolymers of lactide and glycolide (PLGA), polyhydroxy-3-butyrate, collagen, hyaluronic acid, silk, biocellulose, other protein-based polymers, polysaccharides, poly (DTE carbonate), polyarylates, blends of PLLA, PLDA, or PLGA with TMC and other combinations of these polymers.

In one embodiment, the biocompatible mesh is made of thermoplastic resin, polyethylene, ultra-high molecular weight polyethylene, high molecular weight polyolefin, uncoated monofilament polypropylene, polyether ether ketone, polyethylene terephthalate, polytetrafluoroethylene, expanded polytetrafluoroethylene, nylon, silicon, or any combination thereof.

Also provided in this disclosure is a composition comprising, alternatively consisting essentially of, or yet further consisting of a keratinocyte sheet, wherein the keratinocyte sheet is prepared by a process comprising, alternatively consisting essentially of, or yet further consisting of the steps of: obtaining a population of skin cells from a subject; correcting the skin cells ex vivo by integration of a genetic construct encoding functional (e.g., full-length wild-type) human collagen VII (COL7A1) protein; culturing the genetically corrected cells to form the keratinocyte sheet. In some embodiments, the skin cells comprise, alternatively consist essentially of, or yet further consist of keratinocytes. In one embodiment, the skin cells comprise, alternatively consist essentially of, or yet further consist of stem cells. In another embodiment, the stem cells are differentiated to keratinocytes. In some embodiments, the stem cells are differentiated before, after or during the transduction.

Further provided is a pharmaceutical composition comprising, alternatively consisting essentially of, or yet further consisting of a keratinocyte sheet, said keratinocyte sheet comprising, alternatively consisting essentially of, or yet further consisting of skin cells ex vivo integrated with a genetic construct encoding a functional COL7A1 protein. In one aspect, the skin cells are obtained from a subject. In some embodiments, the subject is human. In some embodiments, the skin cells are differentiated from stem cells ex vivo integrated with the genetic construct encoding the functional COL7A1 protein. In one embodiment, the subject suffers from RDEB. In some embodiment, the skin cells or the stem cells are transduced with a virus comprising the genetic construct, wherein the virus comprises retrovirus, lentivirus, or AAV.

In one embodiment, the functional COL7A1 protein is a full-length wild-type human COL7A1 protein. In one aspect, the functional COL7A1 protein comprises, alternatively consists essentially of, or yet further consists of a genetic modification from a full-length wild-type human COL7A1 protein. In another aspect, the functional COL7A1 protein comprises, alternatively consists essentially of, or yet further consists of a genetic modification from a full-length wild-type human COL7A1 protein, wherein the genetic modification is conservative. In a further aspect, the genetic modification comprises, alternatively consists essentially of, or yet further consists of insertion, deletion, and/or mutation.

Also provided in this disclosure is a pharmaceutical composition comprising, alternatively consisting essentially of, or yet further consisting of a corneal cell sheet, said corneal cell comprising corneal cells ex vivo integrated with a genetic construct encoding a functional COL7A1 protein.

In some embodiments, the corneal cells are differentiated from stem cells ex vivo integrated with the genetic construct encoding the functional COL7A1 protein. In another embodiment, the corneal cells are obtained from a subject. In one embodiment, the subject suffers from RDEB. In some embodiments, the subject is human. In some embodiments, the corneal cells or stem cells are transduced with a virus comprising the genetic construct, wherein the virus comprises retrovirus, lentivirus, or AAV. In one embodiment, the retrovirus is LZRSE-virus. In some embodiment, the retrovirus is GalV-pseudotyped. In a further embodiment, the transduced cells meet pre-release criteria of virus transduction efficiency (VTE)>50% and proviral genome copy number (PGCN)≤3.

In one aspect, the functional COL7A1 protein is a full-length wild-type human COL7A1 protein.

In certain embodiments, cells are cultured for 1-21 days. In further embodiments, cells are cultured 7, 14, 21 days or longer. Thus, cells may be cultured under appropriate conditions for 1, 2, 3, 4, 5, 6, 7, 8, 9, 10, 11, 12, 13, 14, 15, 16, 17, 18, 19, 20, 21, 22, 23, 24, 25, 26, 27, 28, 29, or more days. Cells are re-plated, and media and supplements may be added or changed as needed using techniques known in the art.

In certain embodiments, the genetically altered keratinocytes may be cultured under conditions and for sufficient time periods such that at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% of the cells express the C7 transgene.

In one embodiment, the cell compositions of the present disclosure comprise, alternatively consist essentially of, or yet further consist of a genetically altered autologous keratinocyte population, expressing a native human C7 protein in an amount effective for the treatment of EB. Target cell populations are grown in sheets for engraftment onto a subject, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextran, mannitol; proteins; polypeptides or amino acids such as glycine; antioxidants; chelating agents such as EDTA or glutathione; adjuvants (e.g., aluminum hydroxide); and preservatives.

Cell compositions of the present disclosure are administered in a manner appropriate to the treatment of EB. The quantity and frequency of administration will be determined by such factors as the condition of the patient, and the type and severity of the patient's disease, although appropriate dosages may be determined by clinical trials.

The cells may be administered to the subject by methods well known to those of skill in the art, typically in the form of a skin graft. A medical practitioner will be able to determine a suitable administration route for a particular subject based, in part, on the type and location of the disease. The transfected cells may be administered locally to a wound site.

Pharmaceutical preparations of engineered cells for administration to a subject are contemplated by the present invention. One of ordinary skill in the art would be familiar with techniques for administering cells to a subject. Furthermore, one of ordinary skill in the art would be familiar with techniques and pharmaceutical reagents necessary for preparation of these cell sheets prior to administration to a subject.

In certain embodiments of the present invention, the pharmaceutical preparation is an aqueous composition that comprises, alternatively consists essentially of, or yet further consists of the engineered cells that have been modified to over-express C7 and optionally prolyl-4-hydroxylase. In certain embodiments, the transduced cell is prepared using cells that have been obtained from the subject (i.e., autologous cells).

Pharmaceutical compositions of the present invention comprise an effective amount of a solution of the transfected cells in a pharmaceutically acceptable carrier or aqueous medium. As used herein, "pharmaceutical preparation" or "pharmaceutical composition" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the cells, its use in the therapeutic compositions is contemplated. Supplementary active ingredients can also be incorporated into the compositions. For human administration, preparations should meet sterility, pyrogenicity, general safety, and purity standards as required by the FDA Center for Biologics.

A person of ordinary skill in the art would be familiar with techniques for generating sterile solutions for application by any other route. Determination of the size of the cell graft and the number of cells on the graft will be made by one of skill in the art. In certain aspects, multiple doses may be administered over a period of days, weeks, months, or years. A subject may receive, for example, 1, 2, 3, 4, 5, 6, 7, 8, 9, 10, 11, 12, 13, 14, 15, 16, 17, 18, 19, or 20 pieces of graft in the same area or a different area. In one embodiment, the subject may be re-grafted in the same area or a different area. In another embodiment, the subject's biological sample (e.g., keratinocytes or corneal cells) is stored in proper conditions. Once the biological sample is stored, no punch biopsy is necessary if the subject requires a new graft. The stored biological samples can provide sufficient or supplemental information to determine the graft needed by the subject.

When "an effective amount" or "therapeutic amount" is indicated, the precise amount of the compositions of the present disclosure to be administered can be determined by a physician with consideration of individual differences in age, weight, and condition of the patient (subject). It can generally be stated that a cell composition comprising the cells described herein may be administered in the amount of 1-100, $1$-$10^3$, $1$-$10^4$, $1$-$10^5$, $1$-$10^6$, $1$-$10^7$, or more than $10^7$ cells, including all integer values within those ranges. Cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments of the present disclosure, keratinocytes that are genetically engineered using the methods described herein, or other methods known in the art, are administered to a patient in conjunction with (e.g., before, simultaneously, or following) any number of relevant treatment modalities.

WORKING EXAMPLES

The following examples are put forth so as to provide those of ordinary skill in the art with a complete disclosure and description of how to make and use the present invention and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Cell Reprogramming of Autologous Cells as Treatment for Recessive Dystrophic Epidermolysis Bullosa (RDEB).

Recessive Dystrophic Epidermolysis Bullosa (RDEB) is a severe blistering skin disease caused by loss of function mutations of COL7A1, the gene coding for type VII collagen (C7). C7 is the primary component of anchoring fibrils (AF), which stabilize the epidermal basement membrane zone (BMZ) to the dermis. C7 performs this function through the use of multiple domains, including an amino terminal non-collagenous NC1 domain which binds BMZ ligands, a central collagenous domain, which assembles into a triple helix, and an NC2 domain, which catalyzes C7 assembly into AFs. Loss of these functional C7 domains in RDEB results in severe BMZ separation. This produces extensive and painful blistering, erosions, and scarring which in turn can lead to an aggressive and often lethal form of SCC appearing in the second and third decades. Despite advances in the molecular diagnosis of this disease, current therapy is limited to palliative care. Clinical trials of allogeneic fibroblasts (Venugopal et al, *J. Am. Acad. Dermatol.* 2013; 69(6):898-908), bone marrow transplantation (Wagner et al, *N. Engl. J. Med.* 2010; 363(7):629-639), intradermal and intravenous delivery of bone marrow-derived mesenchymal stromal cells (Conget et al, *Cytotherapy* 2010; 12(3):429-431; Petrof et al, *J Investig. Dermatol.* 2015; 135(9):2319-2321; Gorell et al, *Pediatr. Dermatol.* 2015; 32 (2):220-225) and skin substitutes (Falabella et al, *Arch Dermatol.* 2000; 136(10):1225-342) have been conducted with variable rates of efficacy and safety. Preclinical studies have explored potential treatment modalities, including intravenous and topical C7, induced pluripotent stem cells, and aminoglycosides.

Gene therapy is a potentially powerful tool for treatment of monogenic diseases such as RDEB. However, serious safety concerns were raised following gene transfer in patients with severe combined immunodeficiency and Wiskott-Aldrich syndrome. Although insertional mutagenesis still remains a potential concern, an advantage of cutaneous gene therapy is the ability to clinically evaluate for neoplasms more easily due to the superficial placement of the grafted tissue. Moreover, genetically modified skin grafts have been successfully used to treat one patient with junctional EB, with long-term correction and without adverse side effects. The platform for long-term C7 expression in regenerated human epidermis was established to be grafted onto immunodeficient mice (Siprashvili et al, *Hum. Gene Ther.*, 2010, 21(10):1299-1310). This disclosure now provides the results of a Phase I clinical trial of ex vivo gene transfer of LZRSE-COL7A1 Engineered Autologous Epidermal Sheets (LEAES) grafted onto subjects with severe RDEB.

Clinical Results

Figure 3:
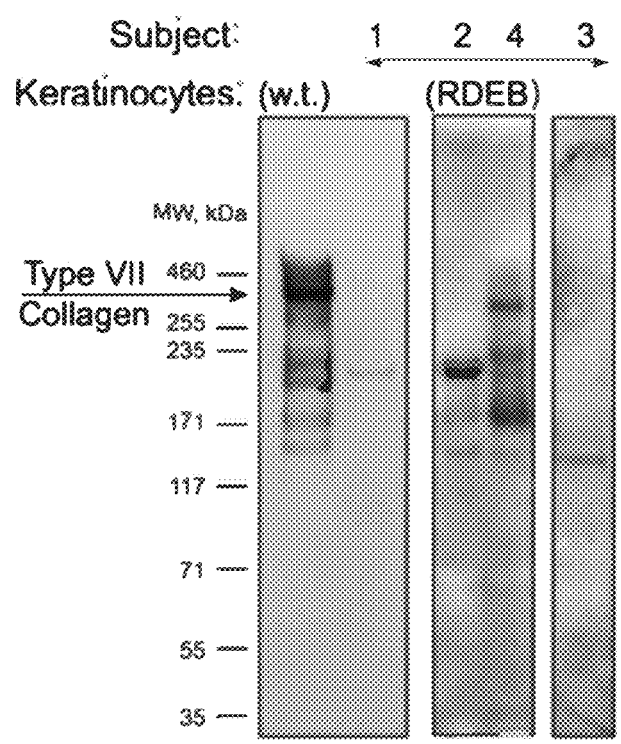
FIG. 3. Western blot analyses of cultured KC supernatant using anti type VII collagen polyclonal antibody specific to NC1 domain. Note truncated C7 protein expression containing NC1 domain in all subjects enrolled in the trial.

Subjects and Treatment. Out of 38 subjects screened, 8 were consented in the study and 4 subjects were enrolled and received grafts (FIG. 2). Subjects carried various compound heterozygous COL7A1 mutations resulting in expression of truncated C7 (NC1 domain) which was detected in keratinocyte medium by Western blot (FIG. 3), but not in tissue by IIF (FIG. 1F, FIG. 5B, 6B, 7B, 8B, 12). All subjects were male, with an average age of 23 (range: 18-32), and an affected total body surface involvement from 4%-30%. Each had severe disease with extracutaneous manifestations, including a history of anemia, esophageal strictures, and pseudosyndactyly (Table 1).

Primary RDEB keratinocytes were isolated from unwounded skin and transduced with LZRSE-COL7A1 retroviral vector with an average of 70% efficiency and 0.8 proviral genome copies per cell (FIG. 1B-D). Five scarred and/or eroded wounds and one induced wound were grafted on each patient. The majority of grafted chronic wounds had been present for >5 years (Table 3). All 24 grafts were serially monitored for percent wound healing, infection, pain, and pruritus.

Figure 10:
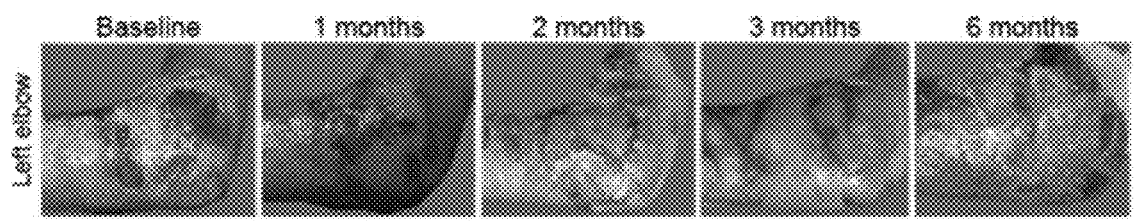
FIG. 10. Clinical representation of uncorrected wounds from subject 4. Characteristic spontaneous blisters development in untreated wounds.

Efficacy. All subjects reported improved wound healing and skin strength as well as decreased pain and itch in graft sites. Grafts showed decreased blistering compared with baseline; representative photos from each subject are shown (FIG. 1E, FIGS. 5A, 6A, 7A, 8A, 12). In contrast, untreated wounds displayed continual blister formation (FIG. 10).

At 1 month post transplantation, 20/24 wounds (83%) showed ≥75% healing while only 4 wounds showed 50%-74% healing (Table 3). At 3 months, 21/24 (87%) wounds were ≥75% healed, while 3/24 (13%) were 50%-74% healed (Table 3). At 6 months, 16/24 (67%) were ≥75% healed, 5/24 (21%) were 50%-75% healed, and only 3/24 (13%) grafted sites displayed blisters and were considered graft failures (0%-49% healed).

The molecular analyses of LEAES grafts revealed robust C7 expression in 9/10 (90%) samples at 3 months and in 8/12 (66%) at 6 months. IIF analysis of LEAES showed appropriate localization of C7 at the epidermal-dermal junction (FIG. 1F, FIGS. 5B, 6B, 7B, 8B, 12) in contrast to the uncorrected skin control. LEAES grafts showed fully differentiated epidermis with spinous and granular layers which were positive for epidermal markers keratin 14, keratin 1, and loricrin resembling normal skin (FIG. 1F, FIGS. 5B, 6B, 7B, 8B, 12). Among negative samples, C7 was undetectable in analyzed biopsies obtained from subject 2 at 6 months; however, anchoring fibrils (AF) were present in a parallel biopsy. At 6 months, C7 was identified in subject 4 using antibodies specific to the NC1 domain (FIG. 1F).

In order to assess molecular structure of the BMZ in corrected samples, biopsies obtained from LEAES grafts were also analyzed by transmission electron microscopy (Methods). At 3 months, 5/7 samples (71%) revealed morphologically normal appearance and frequency of NC2 reactive AF (FIG. 1G). At 6 months, AFs were detected in 4/12 (33%) biopsies, with no AF detected in biopsies obtained from subject 4 (FIG. 1G).

Safety. No serious adverse events were reported. Graft site pruritus (n=3) followed by increased graft site drainage (n=2) were the most common adverse events (Grade 1 or 2) and no clinical signs of malignancy were noted. RCR and cytotoxic T cell assays were negative at all time-points (Table 2).

Increased wound drainage was seen in 2/24 wounds, however no signs of infection including lack of erythema, edema, pain, or tenderness were noted at the sites. At 6 months, site Z for subject 3 had wound colonization (Grade 2) and was considered a graft failure (Table 3). Pruritus was noted at 3/24 graft sites and 2 perigraft areas (Grade 1).

Figure 11A:
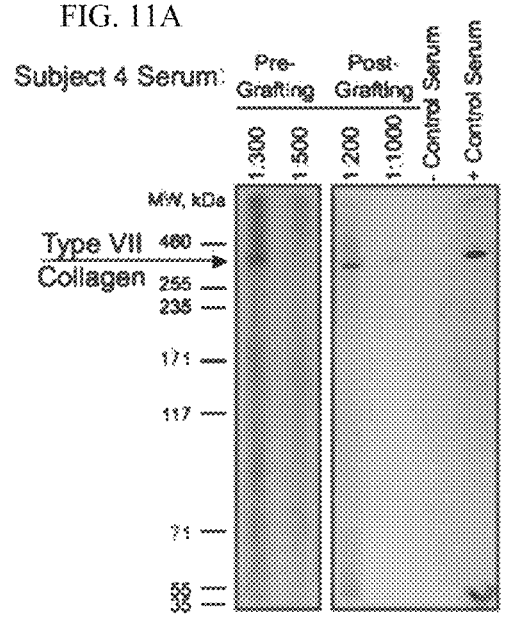
FIG. 11A-11B. Subject 4 serum reactivity to type VII collagen.
Figure 11B:
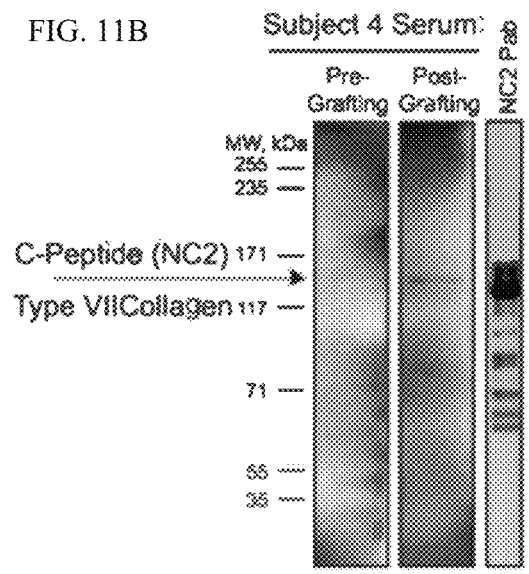

C7 immune responses were closely monitored throughout the study. No subjects had systemic autoimmune symptoms or increased blistering outside of grafted areas. In subject 1, no circulating or tissue bound antibodies were observed by IIF or DIF (Table 2). Subject 2 at 3 months showed 1+ (mild) linear IgG, IgM, IgA, without complement on DIF analysis of 2 wounds (A and E). These immunoreactants were not observed 6 months post grafting. Subject 3 showed transient elevation of linear serum IgA (1:320) at month 3 on IIF with only trace to 1+ linear tissue staining of IgM and IgA at month 6 on DIF. In contrast, subject 4 revealed a 1:160 titer of circulating linear IgG antibodies at months 1 and 3 on IIF along with 1 to 2+ IgG, IgA, C3, and IgM staining detected in 3 grafts at month 3 by DIF (Table 2). However, no systemic autoimmune symptoms or increased blistering outside of grafts were noted and C7-specific cytotoxic T cell assay results were negative. At month 6, serum antibody IgG and C3 levels were reduced (1:40) with no tissue bound immune complexes detected at grafts (Table 2). Following the discovery of the subepidermal linear immune deposits in subject 4, we reassessed subject 4's baseline plasma anti-C7 antibody levels using Western blot analysis of the purified C7 protein. In contrast to the negative baseline IIF data, Western blot analysis showed that both baseline (1:300) and 3 months post grafting serum (1:1000) was reactive to purified C7, indicating that subject 4 was sensitized to exogenous C7 prior to graft placement (FIG. 11A). Subject 4's serum antibody reactivity was confirmed within a previously characterized carboxyl-terminal C7 pepsin fragment, both before and after graft placement (FIG. 11B).

Figure 12:
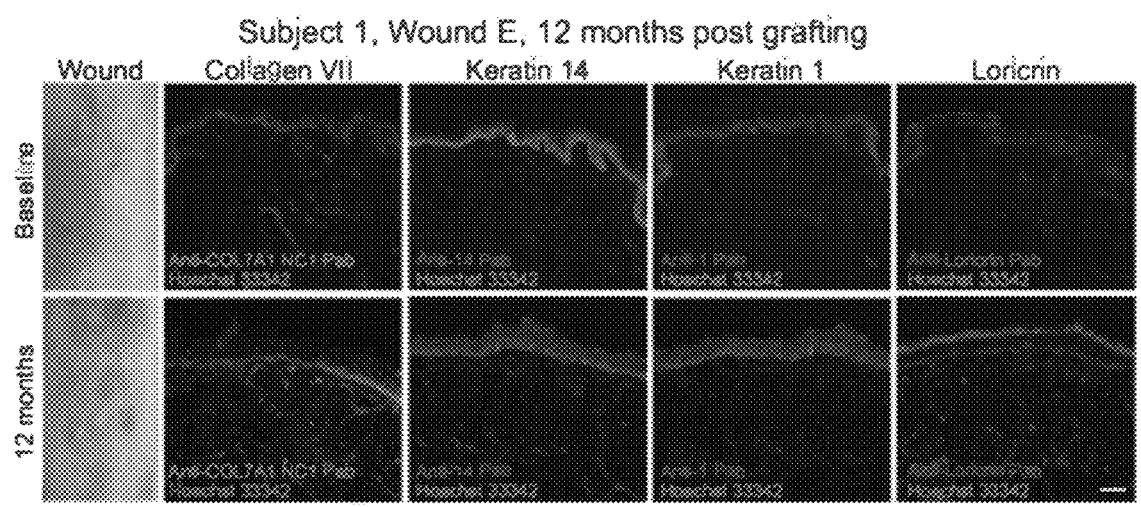
FIG. 12. Subject 1 wounds prior and 12 months post grafting. Clinical representation of wounds at baseline and 12 months post grafting. IIF analyses of type VII collagen expression in skin grafts. Anti-type VII collagen NC1 Pab (green); Hoechst 33342 nuclei (blue); keratin 14 (anti-K14 Pab, orange); keratin 1 (anti-K1 Pab, orange) and loricrin (anti-loricrin Pab, orange). Note linear green staining of type VII collagen at the dermal-epidermal junction of the corrected tissue graft. Scale bar, 100 μm.

Discussion. Genetic correction of RDEB imposes a substantial challenge as it requires efficient delivery of a large transgene encompassing >9 kb COL7A1 cDNA. Here, the disclosure provides the in-human study of genetically corrected autologous epidermal keratinocyte grafting with encouraging efficacy and acceptable safety in 4 subjects with RDEB. Genetically corrected epidermal cells regenerated a functional, self-renewing epidermis in over 67% of grafted sites tested at 6 months post grafting with C7 detectable up to one year for one subject (FIG. 12). This was a noticeable improvement over allogenic keratinocyte grafts where only 2/9 (22%) of chronic wounds were healed at 18 weeks. LEAES grafts also produced better wound healing outcomes compared with allogeneic fibroblast injections, which showed some initial improvement in wound healing but no long term difference compared with placebo, or intradermal or intravenous injections of BM-MSC. A case report of gene therapy for junctional Epidermolysis Bullosa, using a similar methodology, indicated correction for up to 6 years, providing precedence for the long-term therapeutic effect. The six months continued C7 expression we see in our LEAES grafts spans the duration of 6 epidermal turnover cycles, implying that we have successfully targeted stem cells with our gene transfer technique.

In our study, improved wound healing and increased skin durability were directly associated with detectable full-length C7 production and AF formation at the BMZ. While absent prior to grafting, both were present at each study time point, albeit detected with a variable efficiency: 66-90% for C7 expression and 33-71% for AF formation. The biopsy sampling variability could be attributed to either a heterogeneous population of the corrected epidermal cells or to a partial graft uptake. In some embodiments, the graft area can be the area where the subject felt would be beneficial to their quality of life. However, during the critical first few days of graft placement, some of the areas were difficult to immobilize or to protect against mechanical friction (e.g. subject 2's lower back site E, left shoulder site B, Table 3, posterior shoulder site D, FIG. 6A). Furthermore, a shorter immobilization time post grafting as observed may negatively affect graft uptake, as indicated by overall reduced wound healing and absence of detectable C7 by IF in sampled biopsies at six months for subject 2, as the subject had the shortest post transplantation immobilization compared to the other study participants (Table 1). Moreover, although induced wounds displayed good healing capacity, they showed the least C7 expression. It's possible that, without a destructive method such as electrocautery, residual non-corrected wound bed keratinocytes could have disrupted the establishment of overlying LEAES grafts. These findings suggest that improved wound bed preparation techniques which more efficiently ablate wound bed keratinocytes could improve graft uptake.

With regards to safety, few adverse events were reported and those that were seen were all mild. No subjects showed evidence of RCR in blood, or squamous cell carcinoma at grafts at any time points, however long-term monitoring for potential adverse events is ongoing. All molecular replacement approaches, including gene transfer, pose the risk of unwanted immune responses against the therapeutic product, particularly in subjects with null mutations. In this study all subjects expressed a truncated C7 molecule containing the NC1 domain, which is believed to be the antigenic portion of the protein, therefore minimizing the risk of potential immune reaction. No evidence of C7 associated cytotoxic T cell activity was seen at any time point in all subjects during the study. However, IIF and DIF studies in subject 4 revealed BMZ reactive IgG at one and three months, complement C3 fixation at three months with a lower serum IgG titer at six months post transplantation (Table 2). Although, NC1 domain has been reported as the most antigenic portion of C7, the carboxyl terminal NC2 domain also contains minor antigenic epitopes and presence of anti-C7 autoantibodies in RDEB patients was reported extensively in prior works. Findings that subject 4 had detectable anti-C7 antibodies prior to transplantation using Western blot analysis that was not identified during the screening process with a CLIA-certified IIF assay suggests that more sensitive standardized methods should be developed to assess baseline immune cross-reactivity in future therapeutic studies.

In conclusion, genetically corrected autologous epidermal skin grafts showed increased C7 deposition and reduced blistering in patients with severe RDEB, a patient population having few other specific treatment options. Larger studies involving younger RDEB subjects are planned to assess the long-term efficacy and safety of this approach.

TABLE 1

Baseline Characteristics of Grafted RDEB Gene Therapy Subjects

| Subject # | Age/ Sex | COL7A1 Mutation 1 (Location) | COL7A1 Mutation 2 (Location) | C7 expression by IF[2] | C7 expression by Western blot[3] | EM | Circulating auto-antibodies[4] | BSA | Other RDEB symptoms | History of SCC | Previous allograft | Immobilized post-grafting |
|---|---|---|---|---|---|---|---|---|---|---|---|---|
| 1 | 23 M | c.90delC (exon 2) | c.5048_5051 dup4 (GAAA) (exon 54) | Undetectable NC1 and NC2 | NC1+ | No mature AF; sub-LD split | Negative | 8% | Corneal erosions, esophageal strictures, pseudo-syndactyly, anemia, constipation | No | No | 5 days |
| 2 | 19 M | c.90delC (exon 2) | c.5048_5051 dup4 (GAAA) (exon 54) | Undetectable NC1 and NC2 | NC1+ | No mature AF; sub-LD split | Negative | 10-15% | Corneal erosions, esophageal strictures, pseudo-syndactyly, anemia | No | No | 2 days |
| 3 | 32 M | c.6527dupC (exon 80) | c.7485+5 G > A (intron 98) | Trace NC1 Undetectable NC2 | NC1+ | No mature AF; sub-LD split | Negative | 4% | Esophageal strictures, pseudo-syndactyly, hip fracture, anemia | No | No | 8 days |
| 4 | 18 M | c.8053 C > T (exon 109) | c.7929+(11_26) del16 (intron 106) | Undetectable NC1 and NC2 | NC1+ | No mature AF; sub-LD split | Negative[5] | 25-30% | Corneal erosions, esophageal strictures, pseudo-syndactyly, constipation, osteoporosis, anemia, wheelchair-bound | No | No | 5 days |

[1]BSA denotes estimated wounded body surface area, SCC denotes squamous cell carcinoma, IF denotes immunofluorescence of skin biopsy, EM denotes electron microscopy of skin biopsy, AF denotes anchoring fibrils, LD denotes lamina densa, and C7 denotes type VII collagen
[2]Assessed by LH7.2 for NC1 and LH24 for NC2
[3]Skin biopsy sample evaluated using FNC1 antibody
[4]Determined by serum indirect immunofluorescence on monkey esophagus
[5]Circulating auto-antibodies seen on Western blot at baseline; examined following evidence of immune response post-grafting

TABLE 2

Endpoints for Gene Therapy Graft and Systemic Safety

| | | Systemic Safety Endpoints | | | | Graft Safety Endpoints | | |
|---|---|---|---|---|---|---|---|---|
| Subject # | Visit | Increased blistering outside of grafted areas | Circulating auto-antibodies[1] | RCR[2] | Cytotoxic T cells | Graft Infection | SCC[3] | Direct auto-antibodies[4] |
| 1 | 1 mo | — | — | ND[5] | — | — | — | Site E: — |
|   | 3 mo | — | — | — | — | — | — | Site D: — |
|   |   |   |   |   |   |   |   | Site Z: — |
|   | 6 mo | — | — | — | — | — | — | Site E: — |
|   |   |   |   |   |   |   |   | Site Z: — |
| 2 | 1 mo | — | — | ND | — | — | — | Site D: — |
|   | 3 mo | — | — | — | — | — | — | Site A: 1 + IgG, 1 + IgM |
|   |   |   |   |   |   |   |   | Site B: — |
|   |   |   |   |   |   |   |   | Site E: 2 + IgG, trace IgM |
|   | 6 mo | — | — | — | — | — | — | Site A: — |
|   |   |   |   |   |   |   |   | Site C: — |
|   |   |   |   |   |   |   |   | Site D: — |
| 3 | 1 mo | — | — | ND | — | — | — | ND |
|   | 3 mo | — | 1:320 IgA | — | — | — | — | Site A: — |
|   |   |   |   |   |   |   |   | Site C: — |
|   | 6 mo | — | — | — | — | — | — | Site A: trace IgA, trace to 1 + IgM |

TABLE 2-continued

Endpoints for Gene Therapy Graft and Systemic Safety

| | | Systemic Safety Endpoints | | | | Graft Safety Endpoints | | |
| --- | --- | --- | --- | --- | --- | --- | --- | --- |
| Subject # | Visit | Increased blistering outside of grafted areas | Circulating auto-antibodies[1] | RCR[2] | Cytotoxic T cells | Graft Infection | SCC[3] | Direct auto-antibodies[4] |
| 4 | 1 mo | — | 1:160 IgG | ND | — | — | — | Site B: trace IgM<br>Site D: 1 + IgM |
| | 3 mo | — | 1:160 IgG | | — | — | — | Site D: 1-2 + IgG, 1 + IgA, trace IgM, 1 + focal C3<br>Site E: 1-2 + IgG, 1-2 + IgA, 1+ IgM, 1 + focal C3<br>Site Z: 1 + IgG, 1 + IgA, trace IgM, 1 + focal C3 |
| | 6 mo | — | 1:40 IgG<br>1:40 C3 | — | ND | — | — | Site D: —<br>Site E: — |

[1] By indirect immunofluorescence from serum sample on monkey esophagus, autoantibodies localized to basement membrane zone
[2] RCR replication competent retrovirus present in blood
[3] Clinical evidence of squamous cell carcinoma or other neoplasm on graft sites
[4] By direct immunofluorescence performed on skin biopsy, autoantibodies localized to basement membrane zone
[5] ND denotes not done Methods Study Design. This is a Phase I, open-label clinical trial (NCT01263379). The main study objectives were to obtain safety and efficacy data in RDEB subjects grafted with genetically engineered autologous keratinocytes transduced with a retroviral vector containing the full-length COL7A1 coding sequence (FIG. 1A). Between October 2013 and February 2015, 4 adult RDEB subjects were grafted with LEAES. Data on all subjects are collected with at least six months of follow-up. This study was approved by the Food and Drug Administration (IND #13708) and Stanford IRB (Protocol #14563).

Figure 9:
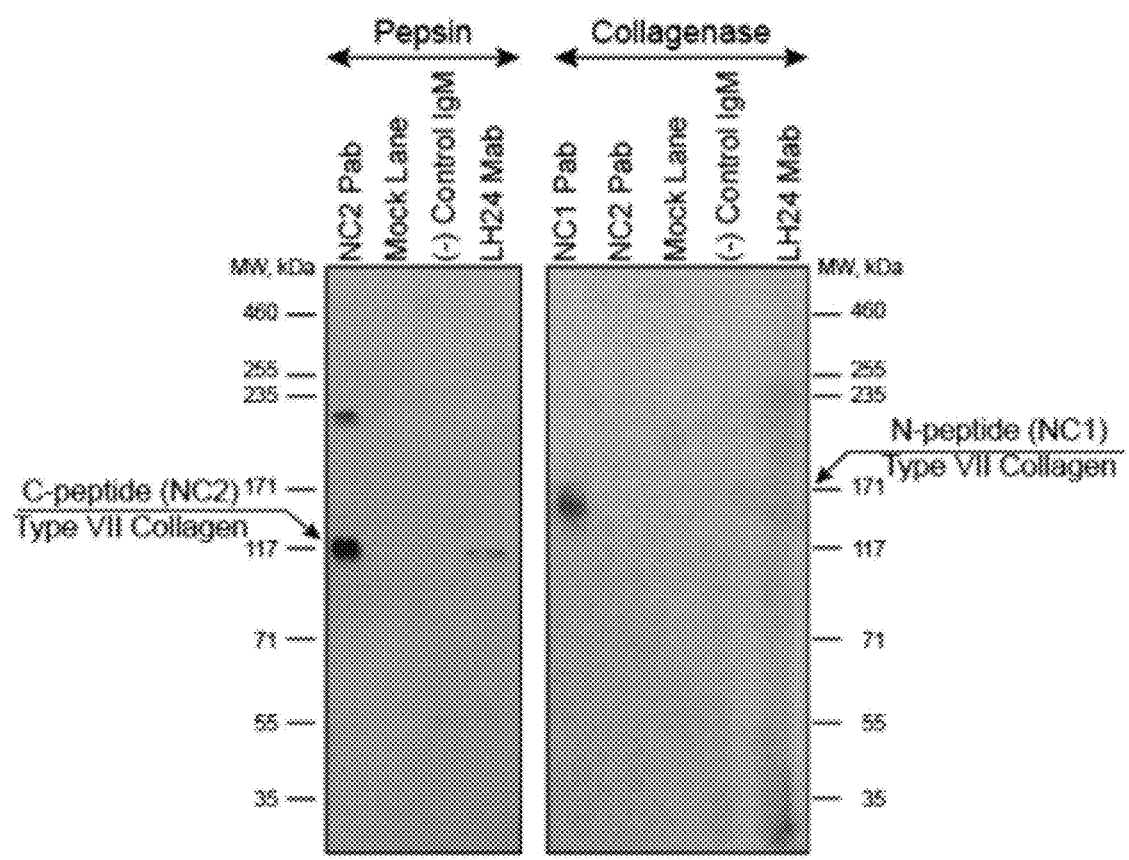
FIG. 9. Anti-C7 LH24 monoclonal antibody characterization. Western blot analysis of the enzymatically digested C7 showing LH24 Mab cross-reactivity to the carboxyl-terminal peptide containing NC2 domain. The NC2 domain presence in the pepsin digested C7 fraction confirmed with NC2 specific pAb (NC2-10) 5. The NC1 domain in collagenase digested C7 fraction identified using FNC1 pAb 6.

Subjects. Subjects were 18 or older and clinically diagnosed with RDEB, had 100 cm$^2$ to 200 cm$^2$ areas of open erosions suitable for LEAES grafting. Subjects were also able to undergo general anesthesia and were selected based on a screening protocol in which RDEB was confirmed via genetic testing (GeneDx, Gaithersburg, MD). Presence of the NC1 domain of C7 was assessed by Western blot of cultured keratinocyte (KC) supernatant and by indirect immunofluorescence microscopy (IIF) of skin biopsy samples. Absence of the full-length C7 and mature AFs in biopsy samples was confirmed by IIF and immuno-electron microscopy (IEM) using LH24 antibody specific to the carboxyl-terminal NC2 domain of C7 (FIG. 9). Circulating and tissue-bound IgG, IgA, IgM, and C3 were analyzed via IIF using serum on primate esophagus and direct immunofluorescence (DIF) of subject biopsy sections, respectively. Subjects with significant non-RDEB medical complications including HIV, hepatitis, systemic infection, or cardiac abnormalities were excluded. Clinically significant anemia was treated prior to grafting.

Figure 4:
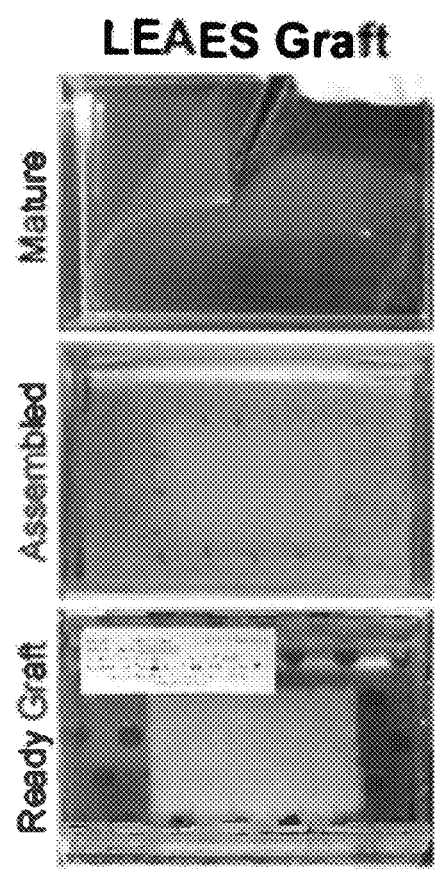
FIG. 4. Mature LEAES prior to harvest, assembled and final LEAES graft shown.
Figure 5A:
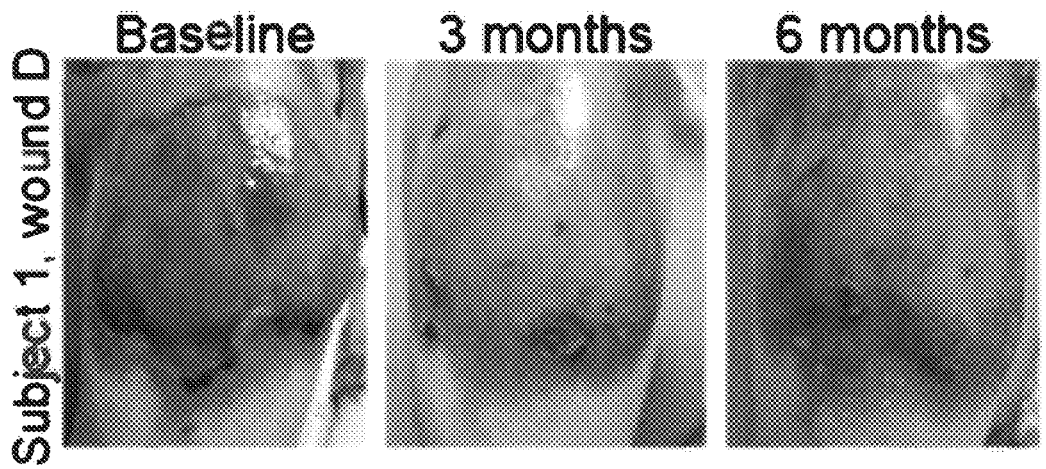
FIG. 5A-5B.
Figure 5B:
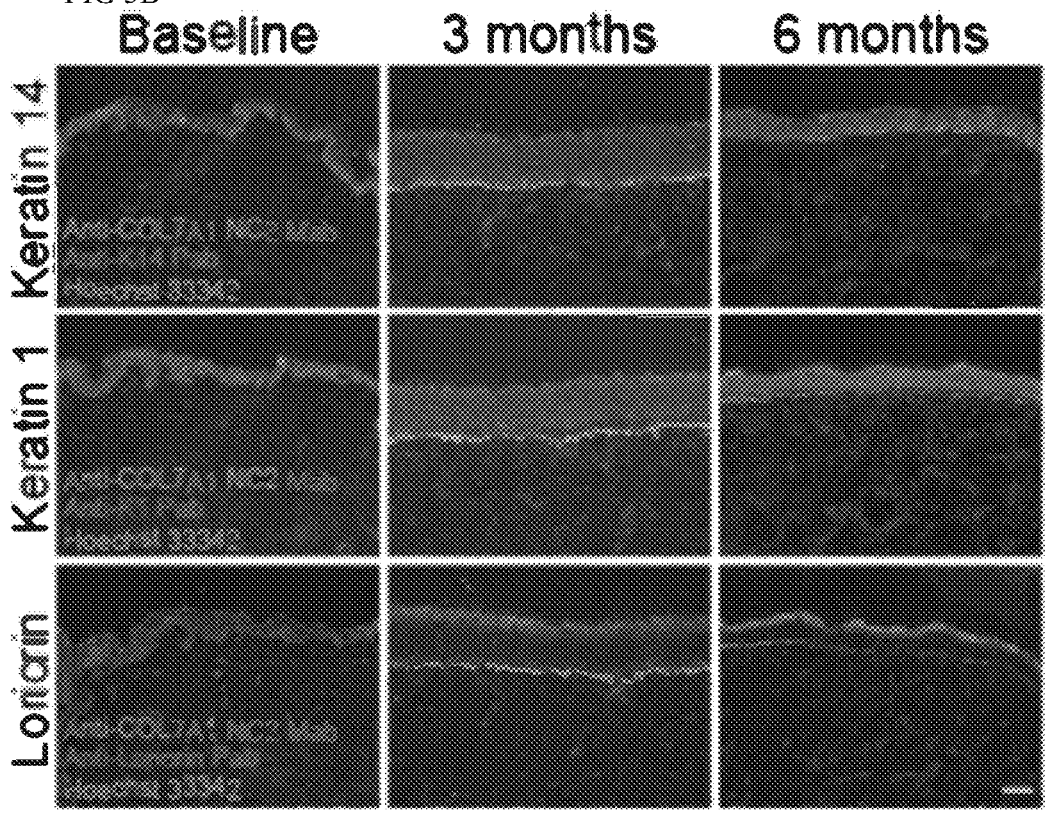
Figure 6A:
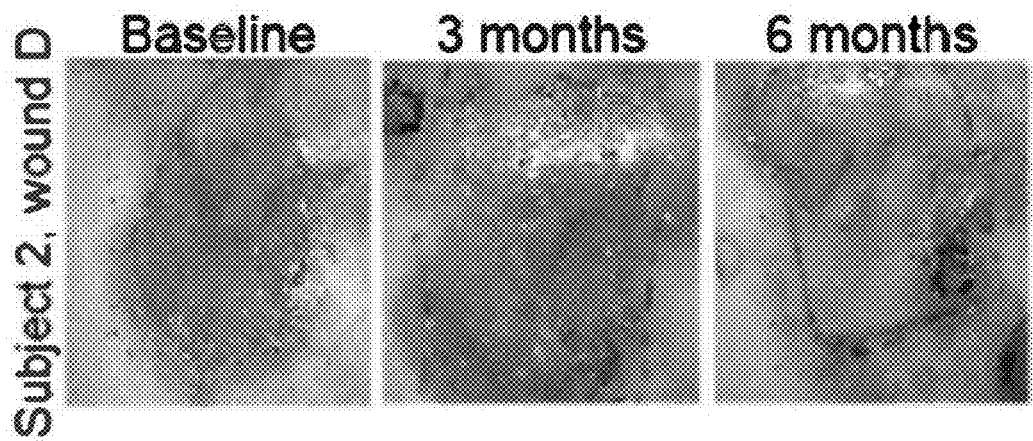
FIG. 6A-6B. Subject 2 wounds prior and post grafting.
Figure 6B:
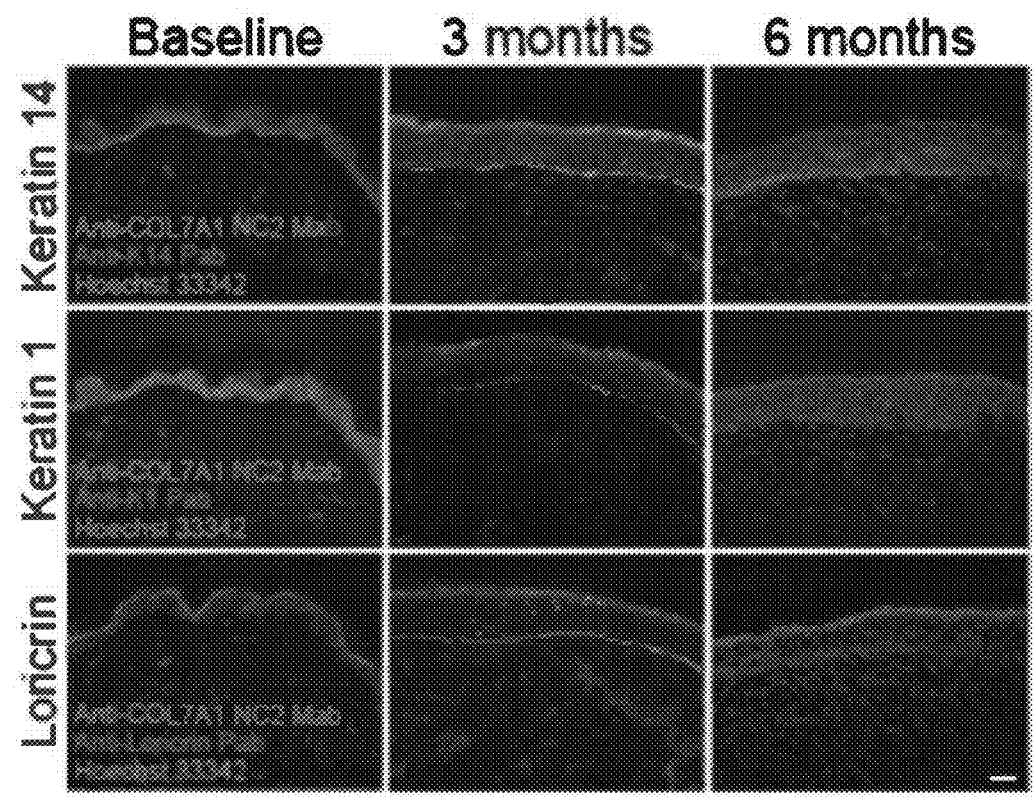
Figure 7A:
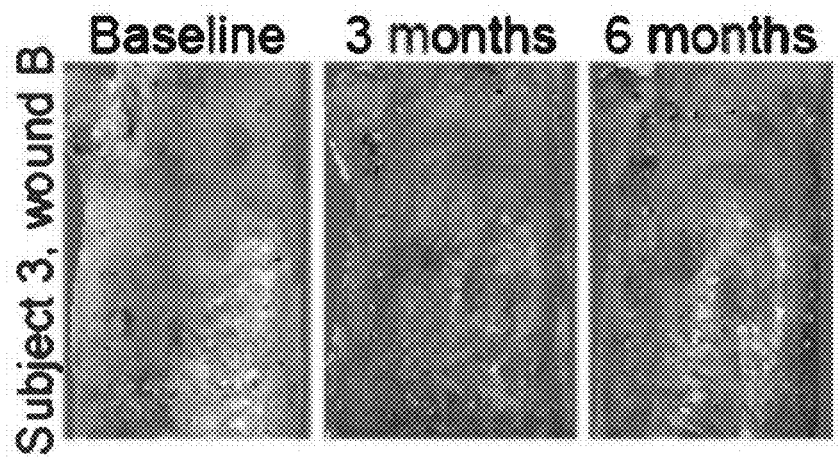
FIG. 7A-7B. Subject 3 wounds prior and post grafting.
Figure 7B:
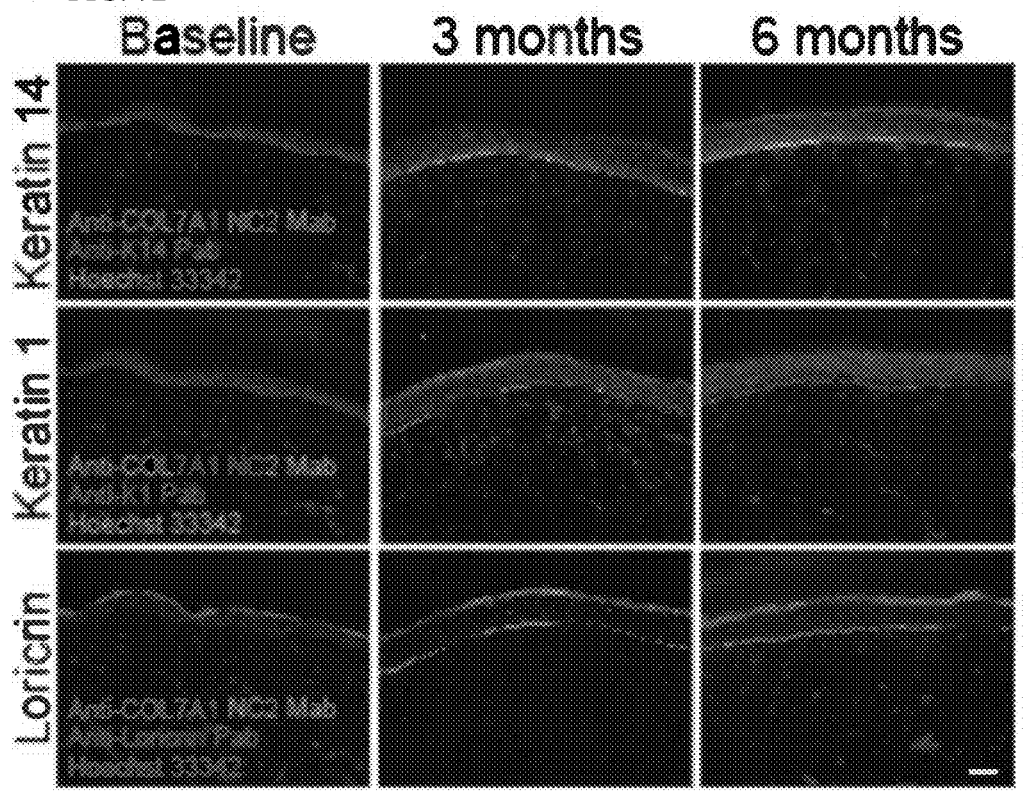
Figure 8A:
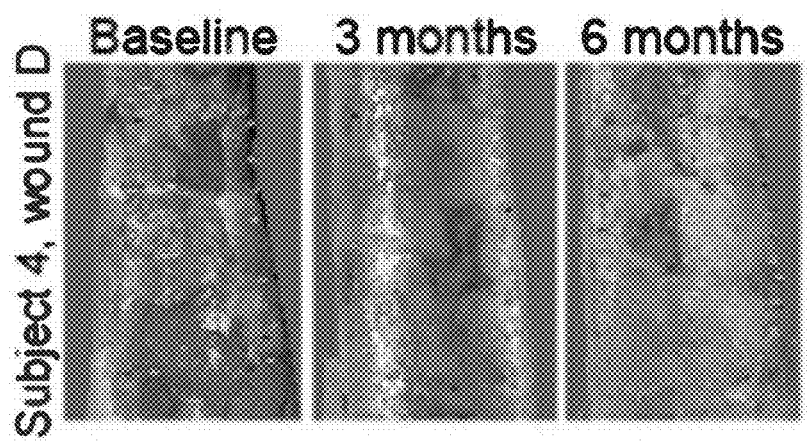
FIG. 8A-8B. Subject 4 wounds prior and post grafting.
Figure 8B:
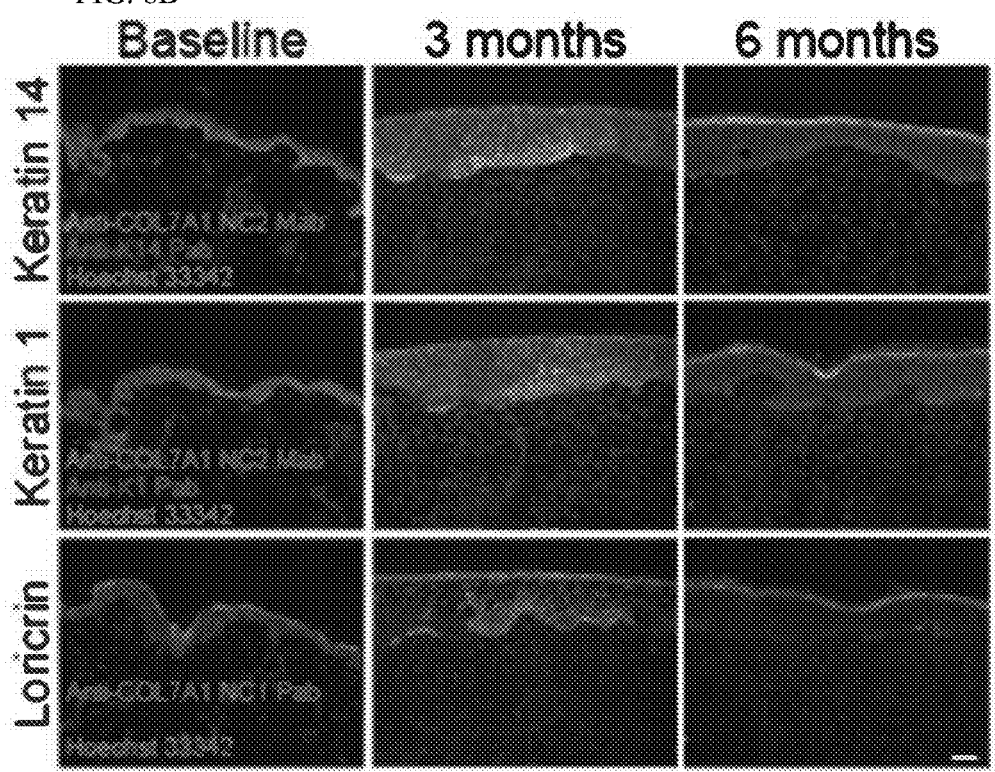

Study Treatment. Two 8 mm punch biopsies were obtained for LEAES manufacture from areas of unwounded, unscarred skin. Baseline blood samples were obtained for CBC, complete metabolic panel (CMP), as well as replication competent retrovirus (RCR) and C7-sensitive cytotoxic T cell assay. Skin biopsy derived autologous keratinocytes were transduced with LZRSE-COL7A1 and used to produce eight LEAES grafts (FIG. 4). Six grafts were applied to uninfected, eroded and/or scarred wound sites that lacked clinical evidence of SCC. Out of six grafted wound sites (A, B, C, D, E, Z, Table 3), one wound was created in each subject at the time of surgery by mechanical friction ("site Z"). Under general anesthesia, wound beds were cauterized to minimize the chance of retained epidermal stem cells. LEAES grafts were affixed to wound beds via dissolvable sutures following wound bed preparation. Subjects 3 and 4 consented to have a small India Ink tattoos placed at the corner of each graft to aide in follow-up graft identification. Grafts were covered with standard wound dressings and topical mupirocin, which were removed 5-7 days post grafting.

End Points and Assessments. Subjects were followed at 1, 3, 6, and 12 months after grafting. At each study visit, serum samples were evaluated for circulating autoantibodies by IIF, for C7-sensitive cytotoxic T cell assay, CBC, and CMP. Presence of RCR in serum was evaluated at 3 and 6 months. At each visit, representative grafts were biopsied to evaluate tissue bound immunoglobulins and complement by DIF, C7 expression by IIF, and presence of anchoring fibrils by IEM. Wounds were assessed clinically and rated as: 100%-75% healed (defined as significant wound healing), 74%-50% healed, 49%-25% healed, less than 25% healed compared with baseline using digital photography and/or the Canfield Vectra camera.

Materials and Reagents

All materials and reagents used during LEAES manufacturing were free of adventitious viruses based on certification of analyses provided by manufacturer. Each lot tissue culture media that included bovine-derived reagents was tested via commercial 9CFR hemadsorption testing for adventitious viruses (American BioResearch, Pullman, WA) and found negative.

RDEB Keratinocyte isolation and expansion. The skin samples were obtained as two 8 mm punch biopsies and transferred into 35 mL biopsy collection medium 50/50A (50% Keratinocyte Medium 154 with human keratinocytes growth supplement (Life Technologies, Carlsbad, CA) and 50% defined keratinocyte serum free media with supplement (Life Technologies, Carlsbad, CA)) with 30 µg/mL amikacin (HIkma Pharmaceuticals, London, United Kingdom), 20 µg/mL vancomycin (Sigma Aldrich, St. Louis, MO) and 0.5 µg/mL amphotericin B (USBiological, Salem, MA). To separate the epidermis from the dermis, the skin sample placed in dispase solution containing 25 caseinolytic units/mL of dispase (Life Technologies, Carlsbad, CA) for 16-20 hours at 5° C. The next day, epidermis was carefully peeled off the dermis and placed in TrypLE Select 10× (Life Technologies, Carlsbad, CA) solution at 37° C. for 20-30 minutes. The solution was spun down at 1200 rpm to obtain a keratinocyte pellet. Cells were washed once with phosphate buffered saline (PBS, Life Technologies, Carlsbad, CA) and keratinocytes were plated on Corning® PureCoat™ Collagen I Mimetic Cultureware (Corning Life Sciences, Tewksbury, MA), in 50/50A media. After keratinocytes reached 60-70% confluence, cells were treated with TrypLE Select 10× and plated for viral transduction. At least $4 \times 10^6$ cells were required to initiate the transduction process.

Keratinocyte correction. The cGMP grade GalV-pseudotyped LZRSE-COL7A1 virus containing full-length COL7A1 cDNA under control of the MLV LTR was produced by Indiana University Vector Production Facility using current Good Manufacturing Practices as described by Siprashvili et al 2010. The map of the pLZRSE-COL7A1 plasmid is depicted in FIG. 13, with its full sequence shown in SEQ ID NO: 1. Viral transduction was performed by overlaying 12 mL viral supernatant for each plate and centrifugation of cells at 1250 rpm and 32° C. for 1 hour. After centrifugation, viral supernatant was removed by washing with PBS and 50/50V medium used for corrected keratinocyte expansion. Transduction was repeated as needed, as long as corrected KC continued to meet pre-release criteria of virus transduction efficiency (VTE)>50% and proviral genome copy number (PGCN)≤3.

Pre-release testing. VTE test. VTE test was performed using IF techniques with anti-type VII collagen monoclonal antibody NP32, NP185 or anti-type VII collagen polyclonal antibody FNC1. Cells were fixed in a solution of methanol/acetone mixture, permeabilized in detergent and incubated with anti-C7 primary antibody for 1 hour at room temperature. After extensive washes, secondary antibody conjugated to Alexa Fluor 555 dye was added and incubated for another 1 hour. Cell nuclei labeled with Hoechst 33342 for 10 minutes, washed, and mounted with Prolong gold antifade reagent (Life Technologies, Carlsbad, CA). VTE was determined by counting the ratio of blue nuclei to C7 positive cells. To meet pre-release criteria, at least 50% of cells were positive for C7 expression.

PGCN test. PGCN test was performed via qPCR analysis of genomic DNA isolated from corrected RDEB KC post retroviral transduction. Genomic DNA was purified from 3×106 corrected cells using Qiagen DNeasy Blood & Tissue Kit (Qiagen, Germany). DNA was quantified using standard spectrophotometric techniques and used for qPCR analysis. Proviral dose was determined using threshold cycle (Ct) of the template and the standard curve of Ct dependence from the amount of plasmid DNA control. The average PGCN was calculated from: PGCN=(TPCN×6.16 pg)/(Ctempl.× 103 pg), where, TPCN=Total proviral copy number. 6.16 pg=Amount of genomic DNA in the somatic cell. Ctempl.=Template amount used in PCR in nanograms. To meet pre-release criteria, no more than 3 proviral genome copy numbers were present on average for every keratinocyte genome.

Sterility test. A sample of culture supernatant was tested for sterility by membrane filtration using the Millipore Steritest system, designed to eliminate potential false negatives from antibiotics present in the culture media (Pacific BioLabs, Hercules, CA). After filtration and washes, the sample was placed in Soybean Case in Digest Medium and Fluid Thioglycollate Medium and incubated for 14 days. Samples were observed for evidence of microbial contamination daily.

Endotoxin test. The sample of the cultured supernatant was assessed via the Limulus Amebocyte Lysate (LAL) QCL-1000 assay (Lonza, Basel, Switzerland) in accordance with manufacturer's recommendations. Results of this test were <1.0 EU/mL in order to satisfy product release requirements.

Mycoplasma test. Cell culture supernatant was tested for mycoplasma using the MycoAlert Mycoplasma Detection Kit (Lonza, Basel, Switzerland) in accordance with manufacturer's requirements. Results of this test were <0.9 in order to satisfy product release requirements.

LEAES initiation and processing. Once corrected keratinocytes reached 100% confluence, the LEAES initiation process was started and growth medium was changed from 50/50V to epidermal sheet production medium DFF31, which consists of Dulbecco's Modified Eagle Medium (Life Technologies, Carlsbad, CA) and F12 medium (Lonza, Basel, Switzerland) containing 10% fetal bovine serum (Lonza, Basel, Switzerland), 36 ng/ml hydrocortisone (Spectrum, New Brunswick, NJ), 25 µg/mL adenine (Sigma Aldrich, St. Louis, MO), 5 µg/mL recombinant human Insulin (Sigma Aldrich, St. Louis, MO), 2 ng/ml liothyronine (Spectrum, New Brunswick, NJ), 5 µg/mL bovine transferrin (Millipore, Billerica, MA), 10 ng/mL recombinant epidermal growth factor (R&D Systems, Minneapolis, MN) and 30 µg/mL amikacin (Hikma Pharmaceuticals, London, United Kingdom), and 20 µg/mL vancomycin (Sigma Aldrich, St. Louis, MO).

LEAES assembly and transportation. LEAES assembly was initiated the day of grafting. Epidermal sheets were released from the surface of the plate by enzymatic digestion with dispase (Life Technologies, Carlsbad, CA) for 20-30 min at 37° C. To remove residual amounts of medium and dispase, epidermal sheets were washed at least 5 times with 50/50VC. It was secured to the matched size petroleum gauze with surgical hemoclips and the basal side was marked with a sterile black suture. Assembled LEAES was submerged in 50/50VC transport medium and sealed with gas permeable sterile film. The LEAES epidermal grafts were then transported to the operating room for transplantation.

Release testing. Gram stain sterility test. On the day of LEAES release, a sample of culture media was sent to the Stanford Hospital Clinical Laboratory for a rapid gram stain test. A negative result of the test was used as a LEAES lot release criteria.

LEAES viability test. Viability testing was performed in which the LEAES sample was incubated with a nuclei dye mixture containing Hoechst 33342 and SYTOX Green stain for 20 minutes. The ratio of SYTOX green stain to Hoechst 33342 stain was calculated at ☐70% to release the product.

Post-release testing. Samples of the cultured medium and LEAES graft were submitted for send-out testing, with expecting test results to be obtained post graft transplantation due to a long duration of the testing process. A safety plan was in place in case these "post-release" test results was out of specification. Post-release criteria included additional sterility testing (see Sterility Test in pre-release testing), RCR testing (Indiana University Vector Production Facility) and mycoplasma testing (Bionique Testing Laboratories, Saranac Lake, NY).

RCR test. A sample of LEAES and LEAES cultured supernatant was subjected to the extended PG-4 S+L− cell plaque assay at Indiana University Vector Production Facility following their recommendations and result of the test "no evidence of RCR" used as release criteria. At baseline, 3 months, and 6 months, blood samples were analyzed by the Indiana University Vector Production Facility to determine the level of GALV envelope (GALV-E) sequences present using a quantitative polymerase chain reaction (Q-PCR). The adequacy of the amount of blood sample was assessed by a second probe and primer set for human apolipoprotein B gene sequences. A standard curve using genomic 12/22/15 8 DNA containing 105, 104, 103, 102, and 10 copies of GALV-E sequence per 0.12 µg of genomic DNA were used as a positive control. Negative controls included untransduced human genomic DNA and water.

Cytotoxic T cell assay. 15 mL of whole blood was collected at baseline, 1 month, 3 months, and 6 months for the cytotoxic T cell assay. Peripheral blood mononuclear cells were isolated from buffy coats or whole blood using Ficoll-Paque (GE Healthcare) density-gradient centrifugation. Adherent monocytes were then recovered after 2-hour incubation in Petri dishes. CD4+ and CD8+ T lymphocytes were purified together using MACS magnetic cell sorting kits (Miltenyi Biotech), by incubating the nonadherent cells with anti-CD4 and anti-CD8 antibodies conjugated to paramagnetic microbeads. A 96-well PVDF-filter plates (Millipore) were coated with monoclonal antibody against IFN-☐ (BD Pharmingen) or IL-4 (BD Pharmingen), blocked using RPMI medium with 5% human AB serum, and washed with serum-free RPMI. CD4+ and CD8+ T lymphocytes ($2 \times 10^5$ cells/well), and ☐☐irradiated monocytes ($2.5 \times 10^4$ cells/well) were co-incubated on the plate in the presence of 20 UI/ml IL-2 for 40 hours at 37° C., in a humidified, 5% $CO^2$ in air incubator. The medium contained either 10 µg/ml of recombinant type VII collagen or 3 µg/ml of Concanavalin A (Sigma) to stimulate the lymphocytes. The plates were washed and the IFN-☐☐ or IL-4 secreted by individual cells were detected in situ by successively reacting each well with biotinylated anti-IFN-☐☐ or anti-IL-4 monoclonal antibody (BD Pharmingen) at 1 µg/ml, following with a 1:1000 dilution of streptavidin-conjugated alkaline phosphatase (Roche). Detection was performed using BCIP/NBT chromogenic substrate (Promega). The reaction was halted by washing with water and spots were counted using a CTL ELISPOT reader. Negative controls were run in parallel using T cells without antigen, and the corresponding scores were subtracted from those of the unknowns.

[Anti-C7 LH24 mAb characterization. LH24 mAb was previously identified to react with epidermal basement membrane 2. Its specific absence in C7 null RDEB patient skin in our study indicated that it recognized an epitope on C7. To further localize LH24 reactivity on the C7 molecule, LH24 reactivity to enzymatic digests of C7 containing NC1 and NC2 domains was tested for by Western blot. NC1 domain containing C7 fragment was produced from digestion of purified C7 with highly purified bacterial collagenase (Worthington) as previously described. 3 NC2 12/22/15 9 containing C7 fragment was produced following pepsin digestion of purified C7 as previously described.

Electron microscopy. A 3 mm skin punch biopsy was prepared for electron microscopy by immersion in 1.5% glutaraldehyde/1.5% paraformaldehyde in Dulbecco's serum free media (SFM) containing 0.05% tannic acid for a minimum of one hour followed by an extensive rinse in SFM, then post-fixation in 1% OsO4 for 60 minutes. The samples were washed in SFM then dehydrated in a graded series of ethanol to 100%, rinsed in propylene oxide and infiltrated in Spurr's epoxy over a total time of two hours, accelerated via microwave energy. Samples were polymerized at 70° C. over 18 hours.

Immuno-electron microscopy. A 3 mm skin punch biopsy sample for immune-electron microscopy were prepared by extensively rinsing in SFM then immersing in mouse IgM LH24 antibody specific to the NC2 region of collagen VII diluted 1:5 in SFM overnight at 4° C., rinsed extensively in SFM, then incubated overnight at 4° C. in Goat anti-mouse IgM ultrasmall colloidal gold conjugate (Aurion) diluted 1:3 in SFM. Following an extensive rinse in SFM the samples were exposed to gold enhancement solution (Nanoprobes) 15 minutes on ice, then rapidly warmed to 25° C. and incubated an additional 5 minutes. The samples were then rinsed with ice-cold SFM, then fixed and embedded as above. Indirect immuno-fluorescence (IIF): Human sera was laid upon monkey esophagus and stained with antibodies directed against human IgA, IgM, IgG, and C3. The signal detected at antibody dilutions of 1:40 and higher considered above background.

Direct immuno-fluorescence (DIF). 12/22/15 10 Tissue was cut at 5 micrometer and stained with fluorophore-conjugated antibodies to human IgA, IgM, IgG, C3, and fibrinogen. Normal controls were run in parallel. C7 expression and AF analysis: A 3 mm skin punch biopsy sample was cut at 8 micrometer and analyzed by IIF using anti-type VII collagen polyclonal antibody FNC1 (raised against NC1 domain of C7) or monoclonal antibody LH24 (NC2 domain of C7). Briefly, sections were fixed in a solution of methanol/acetone mixture, permeabilized in detergent and incubated with anti-C7 primary antibody for 1 hour at room temperature (25° C.). After extensive washes, secondary antibody conjugated to Alexa Fluor 555 or 488 dye was added and incubated for 1 hour. Cell nuclei labeled with Hoechst 33342 for 10 minutes, washed, and mounted with Prolong gold antifade reagent (Life Technologies, Carlsbad, CA). For epidermal markers Keratin 1, Keratin 14 and Loricrin antibodies obtained from Covance (Emeryville, CA). Biopsies were scored positive for C7 expression if continuous linear staining of type VII collagen at the dermal-epidermal junction was detected. Biopsies were scored positive for Anchoring fibrils (AF) if gold conjugate particles were detected representing NC2 domain specific LH24 antibodies at the ultrastructures with characteristic futures of AF including density, thickness, curvature, arching, and looping.

Photography. For subjects 2-4, the Canfield Vectra 3D camera was used to take ~5 images of each graft site from multiple angles. These images were then stitched together to create a comprehensive 3D image. Using Mirror Software (Canfield, Fairfield, NJ) landmarks were selected and numbered to identify corresponding locations on each image, and then melded into a single image. In order to accurately track the graft margins, melded images from follow-up visits were compared to the baseline image, with an overlay of graft outlines from Day 0. Anatomical landmarks (e.g., tattoo dots) were again identified to correctly place the outlines. Additional photographs for subjects 2-4 and all images for subject 1 were obtained as needed with digital photography (Canon Powershot).

EQUIVALENTS

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs. All nucleotide sequences provided herein are presented in the 5' to 3' direction.

The embodiments illustratively described herein may suitably be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement and variation of the embodiments therein herein disclosed may be resorted to by those skilled in the art, and that such modifications, improvements, and variations are considered to be within the scope of this disclosure. The materials, methods, and examples provided here are representative of particular embodiments, are exemplary, and are not intended as limitations on the scope of the disclosure.

The scope of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

What is claimed is:

1. A composition comprising ex vivo differentiated engineered autologous epidermal sheets,
    wherein the ex vivo differentiated engineered autologous epidermal sheets comprise a population of autologous keratinocytes derived from a human patient suffering from Recessive Dystrophic Epidermolysis Bullosa (RDEB) and having one or more mutations in both copies of a human collagen VII A1 (Col7A1) gene that are corrected ex vivo with a retroviral vector comprising a promoter operably linked to a genetic construct encoding a functional collagen VII (COL7A1) to generate a corrected population of autologous keratinocytes;
    wherein the corrected population of autologous keratinocytes is differentiated ex vivo into engineered autologous epidermal sheets with an epidermal sheet production medium, and
    wherein the epidermal sheet production medium comprises Dulbecco's Modified Eagle Medium, F12 medium, 10% fetal bovine serum, 36 ng/ml hydrocortisone, 25 µg/ml adenine, 5 µg/ml insulin, 5 µg/ml transferrin, 10 ng/ml epidermal growth factor, 30 µg/mL amikacin, 20 µg/mL vancomycin, and 2 ng/ml liothyronine.

2. The composition of claim 1, wherein the composition further comprises a pharmaceutically acceptable carrier.

3. The composition of claim 1, wherein the corrected population of autologous keratinocytes meet pre-release criteria for viral transduction efficiency (VTE) of >50% and a proviral genome copy number (PGCN) of less than or equal to 1.5.

4. The composition of claim 1, wherein the genetic construct comprises nucleotides 409 to 11849 of SEQ ID NO: 1.

5. The composition of claim 3, wherein the pre-release criteria for viral transduction efficiency (VTE) is about 70% and the proviral genome copy number (PGCN) is about 0.8.

6. The composition of claim 1, wherein the retroviral vector is selected from Moloney murine leukemia virus (MoMLV), human immunodeficiency virus (HIV), AKR murine leukemia virus (AKR), feline immunodeficiency virus (FIV), or avian leukosis virus (ALV).

7. The composition of claim 1, wherein the retroviral vector is a MoMLV.

8. The composition of claim 1, wherein the retroviral vector is a MoMLV viral vector and the promoter is a MoMLV LTR promoter.

9. The composition of claim 3, wherein the average PGCN is less than 1, or 0.5.

10. The composition of claim 1, further comprising an acellular matrix, a collagen matrix, or a biocompatible mesh.

11. The composition of claim 9, wherein the ex vivo differentiated engineered autologous epidermal sheets are placed on an acellular matrix, a collagen matrix, or a biocompatible mesh.

12. The composition of claim 10, wherein the biocompatible mesh is made of thermoplastic resin, polyethylene, ultra-high molecular weight polyethylene, high molecular weight polyolefin, uncoated monofilament polypropylene, polyether ether ketone, polyethylene terephthalate, polytetrafluoroethylene, expanded polytetrafluoroethylene, nylon, silicon, or any combination thereof.

13. The composition of claim 1, wherein the ex vivo differentiated engineered autologous epidermal sheets are generated by method comprising the steps of:
(a) transducing ex vivo a population of isolated autologous keratinocytes isolated from a population of skin cells obtained from the human patient with a retroviral vector comprising a promoter operably linked to a genetic construct encoding a functional collagen VII (COL7A1) protein to generate a corrected population of autologous keratinocytes expressing a COL7A1 protein, wherein the corrected autologous keratinocytes meet pre-release criteria for viral transduction efficiency (VTE) of >50% and a proviral genome copy number (PGCN) of less than or equal to 1.5 to generate the genetically corrected population of autologous keratinocytes,
wherein the population of isolated autologous keratinocytes are cultured on collagen I peptide in a keratinocyte culture medium without feeder layer cells prior to transduction;
(b) culturing the genetically corrected population of autologous keratinocytes to form an autologous COL7A1 corrected keratinocyte sheet; and
(c) maturing the autologous COL7A1 corrected keratinocyte sheet to form engineered autologous epidermal sheet,
wherein maturing the autologous COL7A1 corrected keratinocyte sheet comprises culturing the autologous COL7A1 corrected keratinocyte sheet in a second culture medium; and
wherein the second culture medium is the epidermal sheet production medium DFF31.

14. A method for differentiating keratinocytes into epidermal sheets ex vivo, the method comprising:
(a) transducing ex vivo a population of isolated autologous keratinocytes isolated from a population of skin cells obtained from a human patient lacking expression of a functional collagen VII A1 (COL7A1) with a retroviral vector comprising a promoter operably linked to a genetic construct encoding the functional COL7A1 to generate a corrected population of autologous keratinocytes expressing the functional COL7A1, wherein the corrected autologous keratinocytes meet pre-release criteria for viral transduction efficiency (VTE) of >50% and a proviral genome copy number (PGCN) of less than or equal to 1.5, and
wherein the population of isolated autologous keratinocytes are cultured in a keratinocyte culture medium without feeder layer cells prior to transduction;
(b) culturing the genetically corrected population of autologous keratinocytes in a first culture medium to form an autologous corrected keratinocyte sheet;
(c) differentiating the autologous corrected keratinocyte sheet into engineered autologous epidermal sheets by culturing the autologous corrected keratinocyte sheet in a second culture medium; wherein the second culture medium is an epidermal sheet production medium comprising Dulbecco's Modified Eagle Medium, F12 medium, 10% fetal bovine serum, 36 ng/ml hydrocortisone, 25 µg/ml adenine, 5 µg/ml insulin, 5 µg/ml transferrin, 10 ng/ml epidermal growth factor, 30 µg/mL amikacin, 20 µg/ml vancomycin, and 2 ng/ml liothyronine; and
(d) assembling the engineered autologous epidermal sheets.

15. The method of claim 14, wherein the first keratinocyte culture medium is a serum-free keratinocyte medium and/or comprises a human keratinocyte growth supplement.

16. The method of claim 14, wherein the human patient suffers from Recessive Dystrophic Epidermolysis Bullosa (RDEB).

17. A composition for differentiating a population of keratinocytes into epidermal sheets ex vivo comprising Dulbecco's Modified Eagle Medium, F12 medium, 10% fetal bovine serum, 36 ng/ml hydrocortisone, 25 µg/ml adenine, 5 µg/ml insulin, 5 µg/ml transferrin, 10 ng/ml epidermal growth factor, 30 µg/mL amikacin, 20 µg/mL vancomycin, and 2 ng/ml liothyronine.

* * * * *

SEQUENCE LISTING

```
Sequence total quantity: 1
SEQ ID NO: 1            moltype = DNA   length = 20326
FEATURE                 Location/Qualifiers
source                  1..20326
                        mol_type = other DNA
                        organism = synthetic construct
SEQUENCE: 1
cccgaaaagt gccaccagct ttgctcttag gagtttccta atacatccca aactcaaata   60
tataaagcat ttgacttgtt ctatgcccta ggggggcgggg ggaagctaag ccagcttttt  120
ttaacattta aaatgttaat tccattttaa atgcacagat gttttattt cataagggtt   180
tcaatgtgca tgaatgctgc aatattcctg ttaccaaagc tagtataaat aaaaatagat  240
aaacgtggaa attacttaga gtttctgtca ttaacgtttc cttcctcagt tgacaacata  300
aatgcgctgc tgagaagcca gtttgcatct gtcaggatca atttcccatt atgccagtca  360
tattaattac tagtcaatta gttgatttt attttgaca tatacatgtg aaagacccca   420
cctgtaggtt tggcaagcta gcttaagtaa cgccattttg caaggcatgg aaaaatacat  480
aactgagaat agaaaagttc agatcaaggt caggaacaga tggaacagct gaatatgggc  540
caaacaggat atctgtggta agcagttcct gccccggctc agggccaaga acagatggaa  600
cagctgaata tgggccaaac aggatatctg tggtaagcag ttcctgcccc ggctcagggc  660
caagaacaga tggtccccag atgcggtcca gccctcagca gtttctagag aaccatcaga  720
tgtttccagg gtgcccaag gacctgaaat gaccctgtgc cttatttgaa ctaaccaatc    780
agttcgcttc tcgcttctgt tcgcgcgctt ctgctccccg agctcaataa aagagcccac   840
aaccctcac tcggcgcgcc agtcctccga ttgactgagt cgcccgggta cccgtgtatc   900
caataaaccc tcttgcagtt gcatccgact tgtggtctcg ctgttccttg ggagggtctc   960
ctctgagtga ttgactaccc gtcagcgggg gtctttcatt tgggggctcg tccgggatcg  1020
ggagaccct gcccagggac caccgaccca ccaccgggag gtaagctggc cagcaactta  1080
tctgtgtctg tccgattgtc tagtgtctat gactgatttt atgcgcctgc gtcggtacta  1140
gttagctaac tagctctgta tctggcggac ccgtggtgga actgacgagt tcggaacacc  1200
cggccgcaac cctgggagac gtcccaggga cttcgggggc cgttttttgtg gcccgacctg  1260
agtccaaaaa tcccgatcgt tttggactct ttggtgcacc ccccttagag gagggatatg  1320
tggttctggt aggagacgag aacctaaaac agttcccgcc tccgtctgaa ttttttgcttt  1380
cggtttggga ccgaagccgc gccgcgcgtc ttgtctgctg cagcatcgtt ctgtgttgtc  1440
tctgtctgac tgtgtttctg tatttgtctg aaaatttggg cccgggccag actgttacca  1500
ctcccttaag tttgacctta ggtcactgga aagatgtcga gcggatcgct cacaaccagt  1560
cggtagttgt caagaagaga cgttgggtta ccttctgctc tgcagaatgg ccaaccttta  1620
acgtcggatg gccgcgagac ggcacctta accgagacct catcacccag gttaagatca  1680
aggtcttttc acctggcccg catggacacc cagaccaggt cccctacatc gtgacctggg  1740
aagccttggc ttttgacccc cctccctggg tcaagccctt tgtacaccct aagcctccgc  1800
ctcctcttcc tccatccgcc ccgtctctcc cccttgaacc tcctcgttcg acccccgcctc 1860
gatcctccct ttatccagcc ctcactcctt ctctaggcgc ccccatatgg ccatatgaga  1920
tcttatatgg ggcacccccg cccttgtaa acttccctga ccctgacttg acaagagtta  1980
ctaacagccc ctctctccaa gctcacttac aggctctcta cttagtccag cacgaagtct  2040
ggagacctct ggcggcagcc taccaagaac aactggaccg accggtggta cctcacccctt 2100
accgagtcgg cgacacagtg tgggtccgcc gacaccagac taagaaccta gaacctcgct  2160
ggaaaggacc ttacacagtc ctgctgacca ccccaccgc cctcaaagta gacggcatcg   2220
cagcttggat acacgccgcc cacgtgaagg ctgccgaccc cggggtgga ccatcctcta    2280
gactgccgga tcccagtgtg gtggtacggg aattcaagct taggatgacg ctgcggcttc  2340
tggtggccgc gctctgcgcc gggatcctgg cagaggcgcc ccgagtgcga gcccagcaca  2400
gggagagagt gacctcacg cgccttaacg ccgctgacat tgtgttctta ctggatggct  2460
cctcatccat tggccgcagc aatttccgcg aggtccgcag ctttctcgaa gggctggtgc  2520
tgcctttctc tggagcagca agtgcacagg gtgtgcgctt tgccacagtg cagtacagcg  2580
```

```
atgacccacg gacagagttc ggcctggatg cacttggctc tgggggtgat gtgatccgcg 2640
ccatccgtga gcttagctac aaggggggca cactcgcac aggggctgca attctccatg 2700
tggctgacca tgtcttcctg ccccagctgg cccgacctgg tgtccccaag gtctgcatcc 2760
tgatcacaga cggggaagtcc caggacctgg tggacacagc tgcccaaagg ctgaagggc  2820
aggggtcaa gctatttgct gtgggatca agaatgctga ccctgaggag ctgaagcgag  2880
ttgcctcaca gcccaccagt gacttcttct tcttcgtcaa tgacttcagc atccttgagga 2940
cactactgcc cctcgtttcc cggagagtgt gcacgactgc tggtggcctg cctgtgaccc 3000
gacctccgga tgactcgacc tctgctccac gagacctggt gctgtctgag ccaagcagcc 3060
aatccttgag agtacagtgg acagcggcca gtggccctgt gactggctac aaggtccagt 3120
acactcctct gacggggctg ggacagccac tgccgagtga gcggcaggag gtgaacgtcc 3180
cagctggtga gaccagtgtg cggctgcggg gtctccggcc actgaccgag taccaagtga 3240
ctgtgattgc cctctacgcc aacagcatcg ggaggctgt gagcgggaca gctcggacca 3300
ctgccctaga agggccggaa ctgaccatcc agaataccac agcccacagc ctcctggtgg 3360
cctggcggag tgtgccaggt gccactggct accgtgtgac atggcgggtc ctcagtggta 3420
ggcccacaca gcagcaggag ctgggcccctg gcagggttc agtgttgctg cgtgacttgg 3480
agcctggcac ggactatgag gtgaccgtga gcacccatt tggccgcagt gtggggcccg 3540
ccacttccct gatggctcgc actgacgctt ctgttgagca gaccctgcgc ccggtcatcc 3600
tgggcccccac atccatcctc cttttcctgga acttggtgcc tgaggcccgt ggctaccggt 3660
tggaatggcg gcgtgagact ggcttggagc caccgcagaa ggtgtactg ccctctgatg 3720
tgacccgcta ccagttggat gggctgcagc cgggcactga gtaccgcctc acactctaca 3780
ctctgctgga gggccacgag gtggccaccc ctgcaaccgt ggttcccact ggaccagagc 3840
tgcctgctgag ccctgtaaca gacctgcaag ccaccgagct gcccgggcag tgggtgcgag 3900
tgtcctggag cccagtccct ggtgccaccc agtaccgcat cattgtgcgc agcacccagg 3960
gggtggagcg gaccctggtg cttcctggga gtcagacagc attcgactg gatgacgttc 4020
aggctgggct tagctacact gtgcgggtgt ctgctcgagt gggtccccgt gagggcagtg 4080
ccagtgtcct cactgtccgc cgggagccgg aaactgcatt tgcttgttcca gggctgcggg 4140
ttgtggtgtc agatgcaacg cgagtgaggg tggcctgggg acccgtccct ggagccagtg 4200
gatttcggat tagctggagc acaggcagtg gtccggagtc cagccagaca ctgccccag  4260
actctactgc cacagacatc acagggctgc agcctgaaac cacctaccag gtggctgtgt 4320
cggtactgcg aggcagagag gagggccctg ctgcagtcat cgtggctcga acggacccac 4380
tgggcccagt gaggacggtc catgtgactc aggccagcag ctcatctgtc accattacct 4440
ggaccagggt tcctggcgcc acaggataca gggtttcctg gcactcagcc cacggcccag 4500
agaaatccca gttggtttct ggggaggcca cggtggctga gctggatgga ctggagccag 4560
atactgagta tacggtgcat gtgagggccc atgtggctgg cgtggatggg cccccctgcc 4620
ctgtggttgt gaggactgcc cctgagcctg tgggctgtc gtcgaggctg cagatcctca 4680
atgcttccag cgacgttcta cggatcacct gggtaggggt cactgagcc acagcttaca 4740
gactggcctg gggccggagt gaaggcgcc ccatgaggca ccagtactc caggaaaca  4800
cagactctgc agagatccgg ggtctcgaag gtggagtcag ctactcagtg cgagtgactg 4860
cacttgtcgg ggaccgcgag ggcacacctg tctccattgt tgtcactacg ccgcctgagg 4920
ctccgccagc cctggggacg cttcacgtgg tgcagcgcgg ggagcactcg ctgaggctgc 4980
gctgggagcc ggtgccagga gcgcaggct tccttctgca ctggcaaccct gagggtggcc 5040
aggaacagtc ccgggtcctg gggcccgagc tcagcagcta tcacctggac gggctggagc 5100
cagcgacaca gtaccgcgtg aggctgagtg tcctagggcc ggctggagaa gggccctctg 5160
cagaggtgac tgcgcgcact gagtcacctc gtgttccaag cattgaacta cgtgtggtgg 5220
acacctcgat cgactcggtg actttggcct ggactccagt gtccaggggca tccagctaca 5280
tcctatcctg gcgccactc agaggccctg gccaggaagt gcctgggtcc ccgcagacac 5340
ttccagggat ctcaagctcc cagcgggtga caggggctaga gtcggcgtc tcttacatct 5400
tctccctgac gcctgtcctg gatggtgtgc ggggtcctga ggcatctgtc acacagacgc 5460
cagtgtgccc ccgtggcctg gcggatgtgg tgttcctacc acatgccact caagacaatg 5520
ctcaccgtgc ggaggctacg aggagggtcc tggagcgtct ggtgttggca cttgggcctc 5580
ttgggccaca ggcagttcag gttgcctgtc tgtcttacag tcatcggctc tcccactgt  5640
tcccactgaa tggctcccat gaccttggca ttatcttgca aaggatccgt gacatgccct 5700
acatggaccc aagtgggaac aacctgggca cagccgtggt cacagctcac agatacatgt 5760
tggcaccaga tgctcctggg cgccgccagc acgtaccagg ggtgatggtt ctgctagtgg 5820
atgaaccctt gagaggtgac atattcagcc ccatccgtga ggcccaggct tctgggctta 5880
atgtggtgat gttgggaatg gctgagcgga acccagagca gctgcgtcgc ttggcgccgg 5940
gtatggactc tgtccagacc ttcttcgccg tggatgatgg gccaagcctg gaccaggcag 6000
tcagtggtct ggccacagcc ctgtgtcagg catccttcac tactcagccc cggccagagc 6060
cctgcccagt gtattgtcca aagggccaga aggggggaacc tggagagatg ggcctgagag 6120
gacaagttgg gcctcctggc gaccctggcc tcccgggcag gaccggtgct ccgggcccca 6180
aggggccccc tggaagtgcc actgccaagg gcgagagggg cttccctgga gcagatgggc 6240
gtccaggcag ccctggccgc gccgggaatc tgggaccccc tggagcccct ggcctaaagg 6300
gctctccagg gttgcctggc cctcgtgggg acccgggaga gcgaggacct cgaggcccaa 6360
aggggggagcc gggggctccc ggacaagtca tcggaggtga aggacctggg cttcctggcc 6420
ggaaagggga ccctgaccca tcgggccccc ctgacctcg tggaccactg ggggaccag  6480
gaccccgtgg ccccccaggg cttcctggaa cagccatgaa gggtgacaaa ggcgatcgtg 6540
gggagcgggg tcccctgga ccaggtgaag gtggcattgc tcctgggag cctgggctgc  6600
cgggtcttcc cggaagccct ggaccccaag gcccgttgg ccccctgga aagaaaggag  6660
aaaaaggtga ctctgaggat ggagctccag gcctcccaag acaactgggg tctccgggta 6720
agcagggcc acgggaccct cctggagcta ttggccccaa aggtgaccgg ggctttccag 6780
ggccctgggg tgaggctgga gagaaaggcg aacgtggacc cccaggcccca gcgggatccc 6840
gggggctgcc aggggttgct ggacgtcctg gagccaaggg tcctgaaggg ccaccaggac 6900
ccactggccg ccaaggagag aagggggagc ctggtcgccc tggggaccct gcagtggtgg 6960
gacctgtcgt tgctggaccc aaaggagaaa agggagatgt gggcccgcct ggcccagga  7020
gagctaccgg agtccaaggg aacgggggcc caccggctt ggttcttcct ggagaccctg 7080
gccccaaggg agaccctgga gacgggtc ccattggcct tactggcaga gcaggaccc  7140
caggtgactc agggcctcct ggagagaagg gagaccctgg gcggcctggc ccccaggac  7200
ctgttggccc ccgaggacga gatggtgaag ttggagagaa aggtgacgag ggtcctccgg 7260
gtgacccggg tttgcctgga aaagcaggcg agcgtggcct cgggggca cctggagttc  7320
```

```
gggggcctgt gggtgaaaag ggagaccagg gagatcctgg agaggatgga cgaaatggca   7380
gccctggatc atctggaccc aagggtgacc gtggggagcc gggtccccca ggaccccgg    7440
gacggctggt agacacagga cctggagcca gagagaaggg agagcctggg gaccgcggac   7500
aagagggtcc tcgagggccc aagggtgatc ctggcctccc tggagcccct ggggaaaggg   7560
gcattgaagg gtttcgggga cccccaggcc cacagggga cccaggtgtc cgaggcccag    7620
caggagaaaa gggtgaccgg ggtcccctg gctggatgg ccggagcgga ctggatggga    7680
aaccaggagc cgctgggccc tctgggccga atggtgctgc aggcaaagct ggggacccag   7740
ggagagacgg gcttccaggc ctccgtggag aacagggcct ccctggcccc tctggtcccc   7800
ctggattacc gggaaagcca ggcgaggatg gcaaacctgg cctgaatgga aaaaacggag   7860
aacctgggga ccctggagaa gacggggagga agggagagaa aggagattca ggcgcctctg   7920
ggagagaagg tcgtgatggc cccaagggtg agcgtggagc tcctggtatc cttgacccc    7980
aggggcctcc aggcctccca gggccagtgg gccctcctgg ccagggtttt cctggtgtcc   8040
caggaggcac gggcccaag ggtgaccgtg gggagactgg atccaaaggg gagcagggcc    8100
tccctggaga gcgtggcctg cgaggagagc ctggaagtgt gccgaatgtg gatcggttgc   8160
tggaaactgc tggcatcaag gcatctgccc tgcgggagat cgtggagacc tgggatgaga   8220
gctctggtag cttcctgcct gtgcccgaac ggcgtcgagg cccaagggg gactcaggcg    8280
aacagggccc cccaggcaag gagggcccca tcggctttcc tggagaacgc gggctgaagg   8340
gcgaccgtgg agaccctggc cctcagggac cacctggtct ggccctgg gagagggcc     8400
cccccgggcc ttccggcctt gccggggagc ctggaaagcc tggtattccc gggctcccag   8460
gcagggctgg gggtgtggga gaggcaggaa ggccaggaga gagggagaa cggggagaga   8520
aaggagaacg tggagaacag ggcagagatg gccctcctgg actccctgga acccctgggc   8580
ccccggacc ccctggcccc aaggtgtctg tggatgaagc aggtcctgga ctctctggag    8640
aacagggacc ccctggactc aagggtgcta agggggagcc gggcagcaat ggtgaccaag   8700
gtcccaaagg agacaggggt gtgccaggca tcaaaggaga ccggggagag cctgaccga    8760
ggggtcagga cggcaacccg ggtctaccag gagagcgtgg tatggctggg cctgaaggga   8820
agccgggtct gcagggtcca agaggccccc ctggcccagt gggtggtcat ggagaccctg   8880
gaccacctgg tgcccgggt cttgctggcc ctgcaggacc ccaaggacct tctggcctga   8940
aggggagcc tggagagaca ggacctccag gacgggcct gactggacct actgagctg    9000
tgggacttcc tggacccccc ggcccttcag gccttgtggg tccacaggg tctccaggtt    9060
tgcctggaca agtgggggag acagggaagc cgggagcccc aggtcgagat ggtgccagtg   9120
gaaaagatgg agacagaggg agccctggtg tgccagggtc accaggtctg cctggccctg   9180
tcggacctaa aggagaacct ggccccacgg ggccctgg acaggctgtg gtcgggctcc    9240
ctggagcaaa gggagagaag ggagcccctg gaggccttgc tggagacctg gtgggtgagc   9300
cgggagccaa aggtgaccga ggactgccag ggccgcgagg cgagaaggg gaagctggcc   9360
gtgcagggga gcccggacgg cctgggggaag atggtcagga aggggctcca ggacccaaag   9420
gtttcaaggg tgacccagga gtcggggtcc cgggctcccc tgggcctcct ggccctccag   9480
gtgtgaaggg agatctgggc ctccctggcc tgccggtgc tcctggtgtt gttgggttcc    9540
cgggtcagac aggccctcga ggagagatgg gtcagccagg ccctagtgga gagcgggtc   9600
tggcaggccc cccaggagga gaagaatcc caggaccct ggggccacct ggaccaccgg    9660
ggtcagtggg accacctggg gcctctggac tcaaaggaga caaggagac cctggagtag   9720
ggctgcctgg gccccgaggc gagcgtgggg agccaggcat ccggggtgaa gatggccgcc   9780
ccggccagga gggaccccga ggactcacgg ggccccctgg cagcaggga gagcgtgggg   9840
agaagggtga tgttgggagt gcaggactaa agggtgacaa gggagactca gctgtgatcc   9900
tggggcctcc aggcccacgg ggtgccaagg gggacatggg tgaacgaggg cctcggggct   9960
tggatggtga caaaggacct cggggagaca atgggaccc tggtgacaag ggcagcaagg   10020
gagagcctgg tgacaaggc tcagcccggt tgccaggact gcgtggactc ctgggacccc   10080
agggtcaacc tggtgcagca gggatccctg gtgacccgga atcccagga aaggatggag   10140
tgcctggtat ccgaggagaa aaggagatg ttggcttcat gggtcccgg ggcctcaagg    10200
gtgaacgggg agtgaaggga gccgtgggcc ttgatggaga gaagggagac aagggagaag   10260
ctggtccccc aggccgcccc gggctggcag gacacaaagg agagatgggg gagcctggtg   10320
tgccggggca gtcgggggcc cctggcaagg agggcctgat cggtccaagg ggtgaccgag   10380
gctttgacgg gcagccaggc cccaagggtg accaggcga gaaagggag cggggaaccc    10440
caggaattgg gggcttccca ggcccagtg gaaatgatgg ctctgctggt ccccagggc    10500
cacctggcag tgttggtccc agaggccccg aaggacttca gggccagaag ggtgagcgag   10560
gtccccccgg agagagagtg gtgggggctc ctggggtccc tggagctcct ggcgagagag   10620
gggagcaggg gcggcagggg cctgccggtc ctcgaggcga gaaggagaa gctgcactga   10680
cggaggatga catccggggc tttgtgcgcc aagagatgag tcagcactgt gcctgccagg   10740
gccagttcat cgcatctgga tcacgacccc tccctagtta tgctgcagac actgccggct   10800
cccagctcca tgctgtgcct gtgctccgcg tctctcatgc agaggaggaa gagcgggtac   10860
cccctgagga tgatgagtac tctgaatact ccgagtattc tgtggaggag taccaggacc   10920
ctgaagctcc ttgggatagt gatgacccct gttccctgcc actggatgag ggctcctgca   10980
ctgcctacac cctgcgctgg taccatcggg ctgtgacagg cagcacagag gcctgtcacc   11040
cttttgtcta tggtggctgt ggagggaatg ccaaccgttt tgggacccgt gaggcctgcg   11100
agcgcgctg cccaccccgg gtggtccaga gccagggaac ggtgctacc caggactgag   11160
aattcgcggc cgccagcaca gtggtcgacg ataaaataaa agattttatt tagtctccag   11220
aaaaagggg gaatgaaaga ccccacctgt aggttgca agctagctta agtaacgcca    11280
ttttgcaagg catggaaaaa tacataactg agaatagaa agttcagatc aaggtcagga   11340
acagatggaa cagctgaata tggccaaac aggatatctg tggtaagcag ttcctgcccc    11400
ggctcaagaa caagaacagct gaatatggc caaacaggat atctgtggta            11460
agcagttcct gccccggctc agggccaaga acagatggtc cccagatgcg gtccagccct   11520
cagcagtttc tagagaacca tcagatgttt ccagggtgcc ccaaggacct gaaatgaccc   11580
tgtgccttat ttgaactaac caatcagttc gcttctcgct tctgttgcgcg cgcttctgct   11640
ccccgagctc aataaaagag cccacaaccc ctcactcggg gcgccagtcc tccgattgac   11700
tgagtcgccc ggtacccgt gtatccaata aaccctctcc cagttgcatc cgacttgtgg   11760
tctcgctgtt ccttgggagg gtctcctctg agtgattgac tacccgtcag cgggggtctt   11820
tcacatgcag catgtatcaa aattaatttg gttttttttc ttaagtattt acattaaatg   11880
gccatagttg cattaatgaa tcggccaacg cgcggggaga gcggtttgc gtattggcgc   11940
tcttccgctt cctcgctcac tgactcgctg cgctcggtcg ttcggctgcg gcgagcggta   12000
tcagctcact caaaggcggt aatacggtta ccacagaat caggggataa cgcaggaaag   12060
```

```
aacatgtgag caaaaggcca gcaaaaggcc aggaaccgta aaaaggccgc gttgctggcg    12120
tttttccata ggctccgccc ccctgacgag catcacaaaa atcgacgctc aagtcagagg    12180
tggcgaaacc cgacaggact ataaagatac caggcgtttc ccctggaag ctccctcgtg     12240
cgctctcctg ttccgaccct gccgcttacc ggatacctgt ccgcctttct cccttcggga    12300
agcgtggcgc tttctcatag ctcacgctgt aggtatctca gttcggtgta ggtcgttcgc    12360
tccaagctgg gctgtgtgca cgaaccccc gttcagcccg accgctgcgc cttatccggt     12420
aactatcgtc ttgagtccaa cccggtaaga cacgacttat cgccactggc agcagccact    12480
ggtaacagga ttagcagagc gaggtatgta ggcggtgcta cagagttctt gaagtggtgg    12540
cctaactacg gctacactag aagaacagta tttggtatct gcgctctgct gaagccagtt    12600
accttcggaa aaagagttgg tagctcttga tccggcaaac aaaccaccgc tggtagcggt    12660
ggttttttg tttgcaagca gcagattacg cgcagaaaaa aaggatctca agaagatcct     12720
ttgatctttt ctacggggtc tgacgctcag tggaacgaaa actcacgtta agggattttg    12780
gtcatgagat tatcaaaaag gatcttcacc tagatccttt tgcggccgaa ttagatccag    12840
acatgataag atacattgat gagtttggac aaaccacaac tagaatgcag tgaaaaaaat    12900
gctttatttg tgaaatttgt gatgctattg ctttatttgt aaccattata agctgcaata    12960
aacaagttaa caacaacaat tgcattcatt ttatgtttca ggttcagggg gaggtgtggg    13020
aggtttttta aagcaagtaa aacctctaca aatgtggtat ggctgattat gatcctctag    13080
agtcggtggg cctcggggc gggtgcgggg tcggcgggc cgcccggtc ggcttcggc        13140
ggagccatgg ggtcgtgcgc tcctttcggt cgggcgctgc gggtcgtggg gcgggcgtca    13200
ggcaccgggc ttgcgggtca tgcaccaggt cgcgcggtcc ttcgggcact cgacgtcggc    13260
ggtgacggtg aagccgagcc gctcgtagaa ggggaggttg cgggggggcgcgg aggtctccag 13320
gaaggcgggc accccggcgc gctcggccgc ctccactccg gggagcacga ccggcgctgcc  13380
cagacccttg ccctggtggt cgggcgagac gccgacggtg gccaggaacc acgcgggctc    13440
cttgggccgt tgcggcgcca ggaggccttc catctgttgc tgcgcggcca gccgggaacc    13500
gctcaactcg gccatgcgcg ggccgatctc ggcgaacacc gccccgctt cgacgctctc     13560
cggcgtggtc cagaccgcca ccgcggcgcc gtcgtccgcg accacacct tgccgatgtc     13620
gagcccgacg cgcgtgagga agagttcttg cagctcggtg accgctcga tgtggcggtc    13680
cgggtcgacg gtgtgcgcg tggcggggta gtcggcgaac gcggcggcga gggtgcgtac    13740
ggcccggggg acgtcgtcgc gggtggcgag gcgcaccgtg ggcttgtact cggtcatgga    13800
aggtcgtctc cttgtgaggg gtcagggcg tgggtcaggg gatggtgggg gcaccggtcg    13860
tggcggccga cctgcaggtc gaaaggcccg gagatgagga agaggagaac agcgcggcag   13920
acgtgcgctt ttgaagcgtg cagaatgccg ggctccgga ggaccttcgg gcgcccgccc    13980
cgcccctgag cccgccctg agcccgcccc cggacccacc ccttcccagc ctctgagccc    14040
agaaagcgaa ggagcaaagc tgctattggc cgctgcccca aaggcctacc cgcttccatt    14100
gctcagcggt gctgtccatc tgcacgagac tagtgagacg tgctacttcc atttgtcacg    14160
tcctgcacga cgcgagctgc ggggcggggg ggaacttcct gactaggga ggagtagaag     14220
gtggcgcgaa ggggccacca agaacggag ccggttggcg cctaccggtg gatgtggaat     14280
gtgtgcgagg ccagaggcca cttgtgtagc gccaagtgcc cagcggggct gctaaagcgc    14340
atgctccaga ctgccttggg aaaagcgcct ccctacccg gtagaattaa ttctcatgtt     14400
tgacagctta tcatcgatag atcctcacag gccgcaccca gcttttcttc cgttgcccca    14460
gtagcatctc tgtctggtga ccttgaagag aagaggagg ggtcccgaga atccccatcc     14520
ctaccgtcca gcaaaaggg ggacgaggaa tttgaggcct ggcttgaggc tcaggacgca    14580
aatcttgagg atgttcagcg ggagtttttcc gggctgcgag taattggtga ttaggacgag    14640
gatggttcgg aggatgggga atttttcgac ctggatctgt ctgacagcga ccatgaaggg    14700
gatgagggtg ggggggctgt tggagggggc aggagtctgc actccctgta ttcactgagc    14760
gtcgtcaat aaagatgtct attgatctct tttagtgtga atcatgtctg acgagggggc    14820
aggtacagga cctggaaatg gcctaggaga gaagggagac acatctggac cagaaggctc    14880
cggcggcagt ggacctcaaa gaagagggg tgataaccat ggacgaggac ggggaagagg    14940
acgaggacga ggaggcggaa gaccaggagc cccgggcggc tcaggatcag ggccaagaca    15000
tagagatggt gtccggagag gggaaaaacg tccaagttgc attggctgca aagggaccca    15060
cggtgaaaca ggagcaggaa caggagcggg aggggcagga gcaggaggaa caggagcagg   15120
aggaggggca ggagcaggag gaggggcagg aggggcagga gggcaggag gggcaggagc     15180
aggaggaggg gcaggagcag gaggagggggc aggaggggca ggaggggcag gagcaggagg   15240
aggggcagga gcaggaggag gggcaggagg ggcaggagca ggaggagggg caggagggc     15300
aggaggaggg gcaggaggag gagggggcagg agcaggagg gggcaggag gggcaggagg    15360
aggaggaggg gcaggagggg caggagcagg aggggcagga gcaggaggag gagcaggagg    15420
ggcaggaggg gcaggagggg caggagcagg aggggcagga gcaggaggag gggcaggagg    15480
ggcaggaggg gcaggagcag gaggggcagg agcaggaggg gcaggagcag gaggggcagg    15540
agcaggaggg gcaggagggg caggagcagg aggggcagga ggggcaggag caggagggc     15600
aggaggggca ggagcaggag gaggggcagg aggggcagga gcaggagcag gggcaggagg    15660
ggcaggagca ggaggggcag gaggggcagg agcaggaggg gcaggagggg caggagcagg    15720
aggggcagga ggggcaggag caggaggagg ggcaggagca ggaggggcag gagcaggagg    15780
tggaggccgg ggtcgaggag gcagtggagg ccggggtcga ggaggtagtg gaggccgggg    15840
tcgaggaggt agtggaggcc gccggggtag aggacgtgga agagccaggg ggggaggtcg    15900
tgaaagagcc aggggggagag gtcgtgacg tggagaaaag aggccaggga gtcccagtag     15960
tcagtcatca tcatccgggt ctccaccgcg caggccccct ccaggtagaa ggccattttt    16020
ccaccctgta ggggaagccg attatttga ataccaccaa gaaggtggcc cagatggtga     16080
gcctgacgtg ccccgggag cgatagagca gggccccgca gatgacccag gagaaggccc     16140
aagcactgga ccccgggtc agggtgatgg aggcaggcgc aaaaaaggag ggtggtttgg     16200
aaagcatcgt ggtcaaggag gttccaaccc gaaatttgag aacattgcag aaggtttaag    16260
agctctcctg gctaggagtc acgtagaaag gactaccgac gaaggaactt gggtcgccgg    16320
tgtgttcgta tatggaggta gtaagacctc cctttacaac ctaaggcgag gaactgccct    16380
tgctattcca caatgtcgtc ttcaccatt gagtcgtctc cctttggaa tggccctgg      16440
accccggcca caacctgcc cgctaaggga gtccattgtc tgttattca tggtcttttt    16500
acaaactcat atatttgctg aggttttgaa ggatgcgatt aaggaccttg ttatgacaaa    16560
gcccgctcct acctgcaata tcaggggtgac tgtgtgcagc tttgacgatg gagtagattt    16620
gcctccctgg tttccaccta tggtggaagg ggctgccgcg gagggtgatg acggagatga    16680
cggagatgaa ggaggtgatg gagatgaggg tgaggaaggg caggagtgat gtaacttgtt    16740
aggagacgcc ctcaatcgta ttaaaagccg tgtattcccc cgcactaaag aataaatccc    16800
```

```
cagtagacat catgcgtgct gttggtgtat ttctggccat ctgtcttgtc accattttcg    16860
tcctcccaac atggggcaat tgggcatacc catgttgtca cgtcactcag ctccgcgctc    16920
aacaccttct cgcgttggaa aacattagcg acatttacct ggtgagcaat cagacatgcg    16980
acggctttag cctggcctcc ttaaattcac ctaagaatgg gagcaaccag caggaaaagg    17040
acaagcagcg aaaattcacg cccccttggg aggtggcggc atatgcaaag gatagcactc    17100
ccactctact actgggtatc atatgctgac tgtatatgca tgaggatagc atatgctacc    17160
cggatacaga ttaggatagc atatactacc cagatataga ttaggatagc atatgctacc    17220
cagatataga ttaggatagc ctatgctacc cagatataaa ttaggatagc atatactacc    17280
cagatataga ttaggatagc atatgctacc cagatataga ttaggatagc ctatgctacc    17340
cagatataga ttaggatagc atatgctacc cagatataga ttaggatagc atatgctatc    17400
cagatatttg ggtagtatat gctacccaga tataaattag gatagcatat actaccctaa    17460
tctctattag gatagcatat gctacccgga tacagattag gatagcatat actaccgaga    17520
tatagattag gatagcatat gctacccaga tatagattag gatagcctat gctacccaga    17580
tataaattag gatagcatat actacccaga tatagattag gatagcatat gctacccaga    17640
tatagattag gatagcctat gctacccaga tatagattag gatagcatat gctatccaga    17700
tatttgggta gtatatgcta cccatggcaa cattagccca ccgtgctctc agcgacctcg    17760
tgaatatgag gaccaacaac cctgtgcttg gcgctcaggc gcaagtgtgt gtaatttgtc    17820
ctccagatcg cagcaatcgc gccctatct tggcccgccc acctacttat gcaggtattc    17880
cccggggtgc cattagtggt tttgtgggca agtggtttga ccgcagtggt tagcggggtt    17940
acaatcagcc aagttattac acccttattt tacagtccaa aaccgcaggg cggcgtgtgg    18000
gggctgacgc gtgcccccac tccacaattt caaaaaaaag agtggccact tgtctttgtt    18060
tatgggcccc attggcgtgg agcccgttt aattttcggg ggtgttagag acaaccagtg    18120
gagtccgctg ctgtcggcgt ccactctctt tccccttgtt acaaatagag tgtaacaaca    18180
tggttcacct gtcttggtcc ctgcctggga cacatcttaa taaccccagt atcatattgc    18240
actaggatta tgtgttgccc atagccataa attcgtgtga gatggacatc cagtctttac    18300
ggcttgtccc caccccatgg attctatttg ttaaagatat tcagaatgtt tcattcctac    18360
actagtattt attgcccaag gggtttgtga gggttatatt ggtgtcatag cacaatgcca    18420
ccactgaacc ccccgtccaa attttattct ggggggcgtca cctgaaacct tgttttcgag    18480
cacctcacat acaccttact gttcacaact cagcagttat tctattagct aaacgaagga    18540
gaatgaagaa gcaggcgaag attcaggaga gttcactgcc cgctccttga tcttcagcca    18600
ctgcccttgt gactaaaatg gttcactacc ctcgtggaat cctgacccca tgtaaataaa    18660
accgtgacag ctcatggggt gggagatatc gctgttcctt aggacccttt tactaaccct    18720
aattcgatag catatgcttc ccgttgggta acatatgcta ttgaattagg gttagtctgg    18780
atagtatata ctactacccg ggaagcatat gctacccgtt tagggttaac aaggggggcct    18840
tataaacact attgctaatg ccctcttgag ggtccgctta tcggtagcta cacaggcccc    18900
tctgattgac gttggtgtag cctcccgtag tcttcctggg cccctgggag gtacatgtcc    18960
cccagcattg gtgtaagagc ttcagccaag agttacacat aaaggcaatg ttgtgttgca    19020
gtccacagac tgcaaagtct gctccaggat gaaagccact cagtgttggc aaatgtgcac    19080
atccatttat aaggatgtca actacagtca gagaaccccct ttgtgtttgg tccccccccg    19140
tgtcacatgt ggaacagggc ccagttggca agttgtacca accaactgaa gggattacat    19200
gcactgcccg tgaccaatac aaaacaaaag cgctcctcgt accagcgaag aaggggcaga    19260
gatgccgtag tcaggtttag ttcgtccggc ggcggggggat ctggccgctt taaatcaatc    19320
taaagtatat atgagtaaac ttggtctgac agttaccaat gcttaatcag tgaggcacct    19380
atctcagcga tctgtctatt tcgttcatcc atagttgcct gactcccccgt cgtgtagata    19440
actacgatac gggagggctt accatctggc cccagtgctg caatgatacc gcgagaccca    19500
cgctcaccgg ctccagattt atcagcaata aaccagccag ccggaagggc cgagcgcaga    19560
agtggtcctg caactttatc cgcctccatc cagtctatta attgttgccg ggaagctaga    19620
gtaagtagtt cgccagttaa tagtttgcgc aacgttgttg ccattgctcg aggcatcgtg    19680
gtgtcacgct cgtcgtttgg tatggcttca ttcagctccg gttcccaacg atcaaggcga    19740
gttacatgat cccccatgtt gtgcaaaaaa gcggttagct ccttcggtcc tccgatcgtt    19800
gtcagaagta agttggccgc agtgttatca ctcatggtta tggcagcact gcataattct    19860
cttactgtca tgccatccgt aagatgcttt tctgtgactg gtgagtactc aaccaagtca    19920
ttctgagaat agtgtatgcg gcgaccgagt tgctcttgcc cggcgtcaac acgggataat    19980
accgcgccac atagcagaac tttaaaagtg ctcatcattg gaaaacgttc ttcggggcga    20040
aaactctcaa ggatcttacc gctgttgaga tccagttcga tgtaacccac tcgtgcaccc    20100
aactgatctt cagcatcttt tactttcacc agcgtttctg ggtgagcaaa aacaggaagg    20160
caaaatgccg caaaaaaggg aataagggcg acacggaaat gttgaatact catactcttc    20220
ctttttcaat attattgaag catttatcag ggttattgtc tcatgagcgg atacatattt    20280
gaatgtatt agaaaaataa acaaataggg gttccgcgca catttc          20326
```